United States Patent [19]
Morita et al.

[11] Patent Number: 6,156,343
[45] Date of Patent: Dec. 5, 2000

[54] CONTROLLED RELEASE PREPARATION

[75] Inventors: Ryoichi Morita, Yamatotakada; Mitsutoshi Arahira; Ritsuko Honda, both of Osaka; Yoshiteru Takahashi, Hirakata, all of Japan

[73] Assignee: Akzo Nobel N.V., Arnhern, Netherlands

[21] Appl. No.: 08/860,121

[22] PCT Filed: Dec. 26, 1995

[86] PCT No.: PCT/JP95/02689

§ 371 Date: Jun. 27, 1997

§ 102(e) Date: Jun. 27, 1997

[87] PCT Pub. No.: WO96/19974

PCT Pub. Date: Jul. 4, 1996

[30] Foreign Application Priority Data

| Dec. 27, 1994 | [JP] | Japan | 6-340045 |
| Dec. 28, 1994 | [JP] | Japan | 6-340407 |
| Jan. 31, 1995 | [JP] | Japan | 7-036156 |
| Feb. 17, 1995 | [JP] | Japan | 7-053534 |
| Aug. 7, 1995 | [JP] | Japan | 7-222566 |

[51] Int. Cl.$^7$ ..................................... A61K 9/34
[52] U.S. Cl. .......................... 424/474; 424/408; 424/451; 424/463; 424/474; 424/475; 424/476; 424/479; 424/480; 424/482

[58] Field of Search ..................... 424/451, 480, 424/463, 464, 408, 409, 417–420, 452, 455, 474–476, 479, 482; 514/960, 961–965

[56] References Cited

U.S. PATENT DOCUMENTS

| 4,892,741 | 1/1990 | Ohm et al. | 424/479 |
| 5,320,853 | 6/1994 | Noda et al. | 424/472 |
| 5,340,590 | 8/1994 | Wong et al. | 424/473 |
| 5,698,220 | 12/1997 | Cardinal | 424/451 |

FOREIGN PATENT DOCUMENTS

| 0 250 374 | 12/1987 | European Pat. Off. | A61K 9/52 |
| 11699 | of 1994 | Japan. | |

*Primary Examiner*—Neil S. Levy
*Attorney, Agent, or Firm*—Merchant & Gould P.C.

[57] ABSTRACT

A controlled release preparation consisting of a tablet containing (a) a mixture of a drug and a water-soluble polymer, or a solid dispersion thereof, (b) polyvinylalcohol and (c) one or more salts selected from the group consisting of trisodium citrate, sodium sulfate and sodium chloride, and the tablet being coated with (d) a coating material consisting of a water-insoluble polymer and a water-soluble polymer and/or an enteric polymer, having the intentionally controllable release pattern and release rate of a drug and being suitable for administration of a drug once or twice a day.

21 Claims, 10 Drawing Sheets

CONTROLLED RELEASE PREPARATION

TECHNICAL FIELD

The present invention relates to a novel controlled release preparation. More specifically it relates to a controlled release preparation consisting of a tablet containing (a) a mixture of a drug and a water-soluble polymer or a solid dispersion thereof, (b) polyvinylalcohol and (c) one or more salts selected from a group consisting of trisodium citrate, sodium sulfate and sodium chloride, and the tablet being coated by (d) a coating material consisting of a water-insoluble polymer and a water-soluble polymer and/or an enteric polymer.

BACKGROUND ART

To keep the plasma level of a drug constant for long hours has many merits not only to enhance preventing or curing diseases,but also to reduce administration times of the drug and to improve the compliance of the patient. Therefore, many kinds of controlled release preparations which control drug release rate from the preparation have been developed and used extensively.

For example, in Japanese Patent Publication No. 11699/1995 a tablet in which a core portion containing a drug (nifedipine) is rapidly released and is coated compressively with a coating material consisting of a hydrophilic gelforming polymer and the drug is described. On administration of this tablet once a day the suitable continuation is attained, but it is not satisfied enough and, in addition to that, there is such a problem that it needs two step-compressing procedures to prepare such a tablet. These are troublesome.

Besides, different from the above preparation, membrane-coated granules and membrane-coated tablets, which are prepared by coating the core portion or an uncoated core-tablet containing a drug with a water-insoluble polymer and a water-soluble polymer, and matrix tablets which are prepared by compressing a drug with a water-insoluble polymer or wax, etc. and so on are evaluated. In such preparations, because the drug release rate is reduced with the lapse of time on administration in vivo, the plasma level of the drug is reduced from time to time. There is such a problem that it is difficult to keep the plasma level of the drug for long hours.

Recently the relationship between circadianrhythm and disease has been given attention to and it becomes important to consider the circadianrhythm in the medical treatment.

From the facts mentioned above, the improvement of controlled release preparations has in various respects have been studied.

DISCLOSURE OF THE INVENTION

The object of the present invention is to provide the controlled release preparation in which a drug in the preparation is continuously released for long hours and the prophylaxis and treatment of diseases are expected on administration of the preparation once or twice a day.

As the result that the present inventors extensively engaged in the study to attain the above mentioned object, it is found that a controlled release preparation prepared by coating an uncoated core-tablet that contains (a) a mixture of a drug and a water-soluble polymer, or a solid dispersion thereof, (b) polyvinylalcohol, and (c) one or more salts selected from a group consisting of trisodium citrate, sodium sulfate and sodium chloride, with (d) a coating material which consists of a water-insoluble polymer and a water-soluble polymer and/or an enteric polymer, is suitable for the object of the present invention.

According to the present invention, on administration of the controlled release preparation of this invention to human body, a water-soluble polymer and/or an enteric polymer in a membrane consisting of a water-insoluble polymer and a water-soluble polymer(referred to as a water-soluble pore-forming membrane), a membrane consisting of a water-insoluble polymer and an enteric polymer (referred to as enteric pore-forming membrane) or a membrane consisting of a water-insoluble polymer, a water-soluble polymer and an enteric polymer (referred to as water-soluble enteric pore-forming membrane) are dissolved in gastro-intestinal fluid, pores are formed in the membrane and then via the pores the drug on the surface of the uncoated core-tablet and around there is gradually released. On the other hand, in concert with this, polyvinylalcohol in the uncoated core-tablet swells. By the swelling, the membrane bursts and then the drug in the uncoated core-tablet is freely released. But the uncoated core-tablet becomes gel-matrix, accompanied with the swelling of polyvinyl alcohol and then the drug in it is gradually released.

If necessary, in the controlled release preparation of the present invention in order to keep the plasma level of the drug further, the above controlled release preparation may be coated with a coating material consisting of an enteric polymer (referred to enteric membrane). In order to maintain the plasma level of a drug in the initial stage of administration, if necessary, on the surface of the controlled release preparation or the enteric coated controlled release preparation mentioned above,a mixture of a drug and a water-soluble polymer, or a solid dispersion thereof may be coated.

BRIEF DESCRIPTION OF DRAWINGS

FIGS. 1 and 5 show examples coated on an uncoated core-tablet (1) with a membrane (2) consisting of a water-insoluble polymer and a water-soluble and/or an enteric polymer. FIGS. 2 and 6 show examples further coated on the above membrane (2) with a membrane consisting of an enteric polymer (3). FIGS. 3 and 7 show examples coated on the above membrane (2) with a mixture of a drug and a water-soluble polymer, or a solid dispersion thereof (4), and FIGS. 4 and 8 show examples coated on the above membrane (2) or the above membrane (3) with a membrane (4). FIGS. 1 to 4 show examples in which a drug (shown by black discontinuous phase) and other components (shown by white continuous phase) in an uncoated core-tablet are contained as a mixture, FIGS. 5 to 8 show examples in which a drug and a water-soluble polymer in an uncoated core-tablets are contained as a solid dispersion (a solid dispersion is shown by black continuous phase, other components are shown by white discontinuous phase).

BEST MODE FOR CARRYING OUT THE INVENTION

Figure 1:
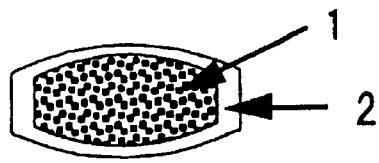
FIGS. 1 to 8 show cross sections of the controlled release preparation.
Figure 2:
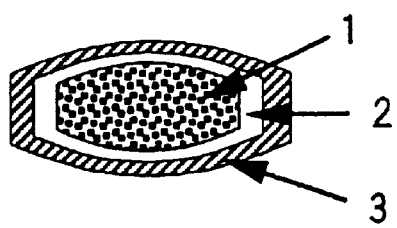
Figure 3:
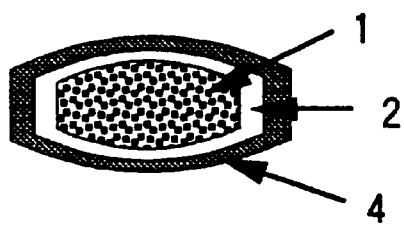
Figure 4:
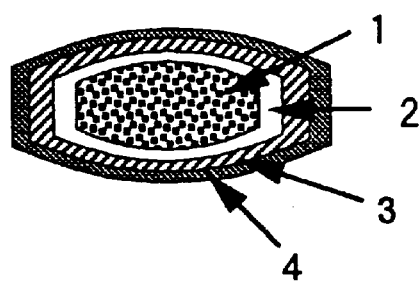
Figure 5:
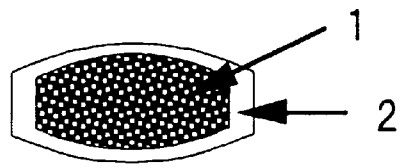
Figure 6:
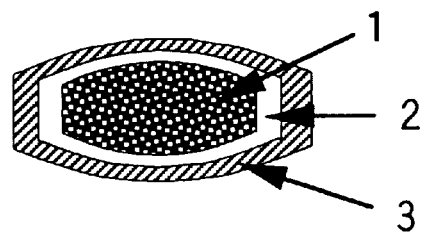
Figure 7:
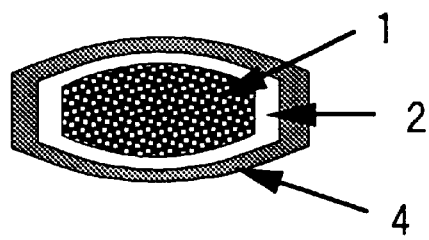
Figure 8:
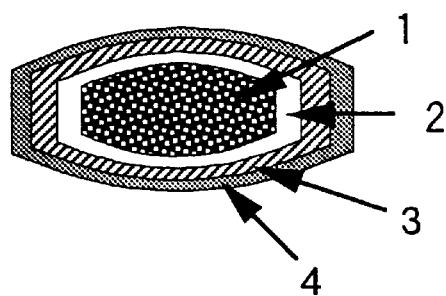

Examples of a water-soluble polymer used in the present invention are illustrated as water-soluble cellulose ethers, polyvinylpyrrolidone, etc.

The above mentioned water-soluble cellulose ethers are ones which by partial substitution of alcohol group which are glucose group in the cellulose, form methyl ether, hydroxypropyl ether and/or hydroxyethyl ether and that are soluble in water.

Examples of the above mentioned water-soluble cellulose ethers are methylcellulose, hydroxypropylcellulose, hydroxypropylmethylcellulose, etc.

Methoxyl group in the methylcellulose is preferably 26.0 to 33.0%, and the methylcellulose described in JP, at page 1070 is preferably used. This compound is sold under a trade name, Metolose SM (produced by Shin-Etsu Chemical Co., Ltd.). In the hydroxypropylcellulose (abbreviated to HPC), hydroxypropoxyl group is preferably 53.4 to 77.5%. This compound is sold under a trade name, Nisso HPC(produced by Nippon Soda Co., Ltd.). In the hydroxypropylmethylcellulose (abbreviated to HPMC), methoxyl and hydroxypropoxyl groups are preferably 19.0 to 30.0% and 4.0 to 12.0% respectively. This compound is sold under such trade names, Metolose 90SH and Metolose 65SH, TC-5 (produced by Shin-Etsu Chemical Co., Ltd.).

The above mentioned polyvinylpyrrolidone is one having a molecular weight of about 25,000 to about 1,200,000, and preferably about 40,000.

The above water-soluble polymer can be used either in the uncoated core-tablet or in the membrane, and also the above water-soluble polymer can be optionally used in the mixture thereof. For example a water-soluble cellulose ether can be used alone or in the mixture of two or more kinds of water-soluble m cellulose ethers, or in the mixture of one or more of water-soluble cellulose ethers and polyvinylpyrrolidone, and in the membrane only a kind of water-soluble cellulose ethers and one or more of them are preferably used. Also, in the membrane a mixture of above water-soluble polymer and an enteric polymer mentioned later may be optionally used.

Among the above water-soluble polymers, hydroxypropylmethylcellulose in which methoxyl and hydroxypropoxyl groups are 28.0 to 30.0% and 7.0 to 12.0% respectively, are preferably used, and especially hydroxypropylmethylcellulose 2910 described in JP, at page 1027 is preferably used.

A water-soluble polymer used in an uncoated core-tablet is mixed for controlling the absorption of a drug and therefore, according to the degree of absorption of a drug the mixing form may be changed. For example, in case that a drug is well absorbed in gastro-intestinal tract, a simple mixture of a drug and a water-soluble polymer may be used, or when a mixture of a drug and other ingredients (b) and (c) is granulated, an aqueous solution of a water-soluble polymer may be used as a binder. Further in the above granulation, a mixture of a drug and a water-soluble polymer may be used instead of a drug alone. On the other hand, when a drug is not well absorbed in gastro-intestinal tract such as a hardly water soluble drug etc., a solid dispersion consisting of a drug and a water-soluble polymer which is prepared by removal of the solvent in an organic solution of a drug and a water-soluble polymer can be used, or a part of said solid dispersion can be used together with the mixture of said water-soluble polymer which can be used as a binder in the granulation in the same manner as above. By forming a hardly water-soluble drug into a solid dispersion, it is possible to improve the absorption of said drug from gastrointestinal tract.

Polyvinylalcohol used in this invention may be a fully hydrolyzed or partially hydrolyzed one, and one having the high swelling ability upon contacting with water is preferably used. For example, polyvinylalcohol of which 93.5 to 97.5% is hydrolyzed is illustrated. This compound is available, for example, under the trade names, Kuraray Poval PVA-613, Kuraray Poval PVA-CST, Kuraray Poval PVA-CSTS, and Kuraray Poval PVA-CS(produced by Kuraray Co., Ltd.).

Trisodium citrate, sodium sulfate and sodium chloride used in this invention can be used in form of anhydride or hydrate thereof respectively. These compounds also can be used as mixtures thereof.

Examples of a water-insoluble polymer used in this invention are ethylcellulose, ethylacrylate methylmethacrylate methacrylic acid trimethylammonium chloride ethyl co-polymer, etc. The above ethylcellulose in which ethoxy group is 46.5 to 51.0% is preferably used. This ethylcellulose is available, for example, under the trade name, Ethocel (produced by Dow Chemical Co., Ltd.). Aminoalkylmethacrylate co-polymer RS as ethylacrylate methylmethacrylate methacrylic acid trimethylammonium chloride ethyl co-polymer is preferably used. This polymer is available, for example, under the trade name, Eudragit RS (produced by Röhm Pharm Co., Ltd.). Among the water-insoluble polymers mentioned above, ethylcellulose in which the ethoxyl group is 46.5 to 51.0% is especially preferable.

Examples of an enteric polymer used in this invention are hydroxypropylmethylcellulose phthalate (abbreviated to HPMCP), hydroxypropylmethylcellulose acetate succinate, carboxymethylethylcellulose, etc. Hydroxypropylmethylcellulose phthalate in which methoxyl, hydroxypropoxyl and carboxybenzoyl groups are 18.0 to 24.0%, 5.0 to 10.0% and 21.0 to 35.0% respectively is preferably used. This phthalate is available, for example, under the trade names, HPMCP HP-55 and HPMCP HP-50 (produced by Shin-Etsu Chemical Co., Ltd.). Hydroxypropylmethylcellulose acetate succinate is a mixed ester of hydroxypropylmethylcellulose with acetic acid and mono succinic acid. The mixed ester in which methoxyl, hydroxypropoxyl, acetyl and succinoyl groups are 12.0 to 28.0%, 4.0 to 23.0%, 2.0 to 16.0% and 4.0 to 28.0% respectively is preferably used. This ester is available, for example, under the trade name, Shin-Etsu AQOAT (produced by Shin-Etsu Chemical Co., Ltd.). Carboxymethylethylcellulose is a mixed ether of cellulose with carboxymethyl and ethyl. The mixed ether in which carboxymethyl and ethoxyl groups are 8.9 to 14.9% and 32.5 to 43.0% respectively is preferably used. This cellulose is available, for example, under the trade name, CMEC (produced by Freund Ind. Co., Ltd.). Also, a mixture of above illustrated enteric polymers may be optionally used.

Among enteric polymers mentioned above, HPMCP in which methoxyl, hydroxypropoxyl and carboxybenzoyl groups are 18.0 to 22.0%, 5.0 to 9.0% and 27.0 to 35.0% respectively is preferably used.

The controlled release preparation of this invention is prepared as follows.

First, a drug, or a drug and a water-soluble polymer of component (a), polyvinylalcohol of component (b) and one or more salts selected from a group consisting of trisodium citrate, sodium sulfate and sodium chloride of component (c) are mixed, and then a mixture of components (a), (b) and (c) are granulated by using an aqueous solution of a water-soluble polymer as a binder to prepare granules containing a drug, or a solution prepared by dissolving a drug and a water-soluble polymer in organic solvent (hereinafter referred to a solid dispersion solution) is sprayed on a mixture of components (b) and (c) and the mixture is dried, or a solid dispersion solution is added to a mixture of components (b) and (c), the resulting mixture is kneaded and the solvent is removed and the residue is crushed to prepare granules containing a drug.

Then the granules prepared above are compressed to prepare uncoated core-tablets.

Further, a water-insoluble polymer and a water-soluble polymer are dispersed or dissolved in water and/or organic solvent (hereinafter referred to as water-soluble pore-forming membrane solution) and the resulting solution is sprayed on the surface of the uncoated core-tablets prepared above and the tablets are dried to prepare a tablet coated with pore-forming membrane (hereinafter referred to as water-soluble pore-forming membrane coated tablet) or a water-insoluble polymer and an enteric polymer are dispersed or dissolved in water and/or organic solvent (hereinafter referred to as enteric pore-forming membrane solution) and the resulting solution is sprayed on the surface of the uncoated core-tablet prepared above and the tablets are dried to prepare a tablet coated with enteric pore-forming membrane (hereinafter referred to as enteric pore-forming membrane coated tablet) or a water-insoluble polymer, a water-soluble polymer and an enteric polymer are dispersed or dissolved in water and/or organic solvent (hereinafter referred to as water-soluble enteric pore-forming membrane solution) and the resulting solution is sprayed on the surface of the uncoated core-tablets prepared above and the tablets are dried to prepare a tablet coated with water-soluble enteric pore-forming membrane (hereinafter referred to as water-soluble enteric pore-forming membrane coated tablet).

Thus, a controlled release preparation of this invention can be prepared.

As another embodiment of this invention, if necessary, an enteric polymer is dissolved or dispersed in water and/or organic solvent (hereinafter referred to as enteric coating solution) and is sprayed on the surface of the controlled release preparation prepared above and the preparation is dried by using the same method as mentioned above to make a coated tablet (hereinafter referred to enteric coated tablet). By making such a preparation, it is possible to maintain the plasma level of a drug for longer hours.

And, if necessary, when on the surface of the above mentioned water-soluble pore-forming membrane coated tablet, enteric pore-forming membrane coated tablet, water-soluble enteric pore-forming membrane coated tablet or enteric membrane coated tablet, a mixture of a drug and a water-soluble polymer or a solid dispersion thereof is coated in the same manner as mentioned above, it is also possible to maintain the plasma level of a drug during the initial stage of administration.

To the above mentioned mixture of polyvinylalcohol and one or more salts selected from a group consisting of trisodium citrate, sodium sulfate and sodium chloride, one or more carriers (excipients) used conventionally in a pharmaceutical preparation such as starch, sucrose, lactose, mannitol, crystalline cellulose, etc., may be admixed, if necessary.

To the above mentioned granules, one or more lubricants such as magnesium stearate, talk, etc. and one or more flowing agents such as light anhydrous silicic acid, hydrated silicon dioxide and synthetic aluminum silicate are mixed optionally. Thus uncoated core-tablets can be prepared.

Diameter of an uncoated core-tablet is normally 2 to 10 mm, preferably 2 to 6 mm and more preferably 5 mm.

The amount of a water-soluble polymer which is added to an uncoated core-tablet in case of using a water-soluble polymer as a binder, is normally 0.01 to 20 weight parts per 1 weight part of a drug, preferably 0.05 to 5 weight parts. In case that a water-soluble polymer is admixed to the mixture of polyvinylalcohol and one or more salts selected from a group consisting of trisodium citrate, sodium sulfate and sodium chloride, the amount of a water-soluble polymer is normally 0.01 to 150 weight parts per 1 weight part of a drug, preferably 0.1 to 30 weight parts.

On the other hand, the amount of a water-soluble polymer is normally 1 to 7 weight parts per 1 weight part of a drug, preferably 1.5 to 3 weight parts when it is used for preparing a solid dispersion.

The organic solvent used for a solid dispersion solution is not limited if the solvent can dissolve both a drug and a water-soluble polymer, and the solvent such as methanol, ethanol, isopropanol, acetone, chloroform, dichloromethane or a mixture thereof can be illustrated. The appropriate amount of the organic solvent is 1.2 to 3 times as much as the amount of a drug and a water-soluble polymer which are soluble in the organic solvent at room temperature.

The amount of polyvinylalcohol in an uncoated core-tablet is normally 0.1 to 400 weight parts per 1 weight part of a drug, preferably 1 to 50 weight parts. The amount of one or more salts selected from a group consisting of trisodium citrate, sodium sulfate and sodium chloride is normally 0.01 to 300 weight parts per 1 weight part of a drug, preferably 0.1 to 50 weight parts.

The amount of a water-insoluble polymer and a water-soluble polymer and/or an enteric polymer used for forming the membrane is normally 5 to 20 weight percent per uncoated core-tablet.

In respect of the ratio of a water-insoluble polymer and a water-soluble polymer and/or an enteric polymer, whether a water-soluble polymer and an enteric polymer are used alone or in combination, its suitable total amount in any way is normally 0.4 to 0.8 weight parts per 1 weight part of a water-insoluble polymer. In addition to a water-insoluble polymer and a water-soluble polymer and/or an enteric polymer, one or more additives such as plasticizers (e.g. triacetin, triethyl citrate, MACROGOL 6,000, etc.) are admixed optionally to the water-soluble pore-forming membrane solution, the enteric pore-forming membrane solution, the water-soluble enteric pore-forming membrane solution and the enteric membrane solution. Its amount is 5 to 40 weight percent per total amount of a water-insoluble polymer and a water-soluble polymer and/or an enteric polymer.

Examples of organic solvent used for a water-soluble pore-forming membrane solution, an enteric pore-forming membrane solution or a water-soluable enteric pore-forming membrane solution, are not limited, and are methanol, ethanol, isopropanol, acetone, chloroform and dichloromethane, and a mixture thereof. In case that a mixture of water and organic solvent is used, it is necessary to choose solvents well miscible with each other.

In preparing enteric membrane-coated tablets, the amount of an enteric polymer is 4 to 12 weight percent per weight of a water-soluble pore-forming membrane-coated tablet, an enteric pore-forming membrane-coated tablet or a water-soluble enteric pore-forming membrane-coated tablet.

In order to maintain the high plasma level of a drug during the initial stage of administration, in case of coating with a drug on the surface of the tablet in the form of a binder or a solid dispersion solution, the amount of a drug in said coating region is 1 to 30 weight percent, preferably 5 to 25 weight percent per total amount of a drug in the controlled release preparation of this invention.

In addition to that, when a drug is unstable to light, to stabilize the drug, for example, hydroxypropylmethylcellulose, and titanium oxide, red ferric oxide, yellow ferric oxide, food yellow No. 4 or No. 5, etc. are dissolved or dispersed in water and/or in organic solvent, and the resulting solution may be sprayed on the controlled release preparation of this invention and the preparation may be dried to prepare the tablet coated with the membrane for protecting from light on the tablet.

The above mentioned method is described on a tablet, but the preparation of this invention is not limited to it, and other dosage forms are included. For example, tablets which are prepared by using an uncoated core-tablet (2 to 6 mm in diameter) may be filled into a capsule with a conventional method to form capsules.

A drug contained in the controlled release preparation of this invention is not limited as long as the therapeutic efficacy of the drug is increased by maintaining the plasma level of the drug for long hours.

The examples are drugs for cardiovascular system (nifedipine, lomerizine hydrochloride, nicardipine hydrochloride, nitroglycerine, isosorbide dinitrate, captopril, delapril hydrochloride, ifenprodil tartrate), drugs for digestive system gastro-intestinal (domperidone, metoclopramide), anti-allergic agents (e.g. emedastine difumarate), antidepressants (e.g. trazodone hydrochloride), analgesics (indomethacin, ibuprofen), antitumors (e.g. altretamine, FUTRAFUL, fluorouracil, etoposide) and so on. The amount of a drug in a tablet is an unit dose as known as effective amount in the drug, and for example when it is administered once a day, one day dose is compounded in the preparation of this invention. Among the above mentioned drugs, the preparation of this invention containing nifedipine which is especially hardly soluble in water, is excellent in gastro-intestinal absorption after oral administration and the continuation of the plasma level of the drug and therefore is useful as a preparation for once a day-administration dosage form.

The preparation of the present invention is orally administered, usually once or twice a day for prophylaxis or treatment of various kinds of diseases.

A drug in the controlled release preparation of this invention is released at least via two steps mentioned below.

First, in the first step a water-soluble polymer and/or an enteric polymer in the water pore-forming membrane, the enteric pore-forming membrane or the water-soluble enteric pore-forming membrane consisting of a water-soluble polymer and a water-insoluble polymer and/or an enteric polymer, dissolve in gastro-intestinal fluid and thereby pores in the coating layer are formed. The gastro-intestinal fluid penetrates into an uncoated core-tablet and a drug in the tablet dissolves and is gradually released. On this occasion it is possible to control the drug release by adding a water-soluble polymer to an uncoated core-tablet. And accompanied with the gradual drug release, a component (b), that is polyvinylalcohol, swells to accelerate the drug release by the gastro-intestinal fluid which penetrates in the tablet, but in this case components (c), trisodium citrate, sodium sulfate and sodium chloride contained in the uncoated core-tablet control the swelling of polyvinylalcohol, and these salts dissolve in gastro-intestinal fluid, and the solution gradually diffuses outside of the coated layer of the tablet, and then the salt concentration results in decrease. Thereafter polyvinylalcohol begins to swell by the gastro-intestinal fluid.

In the second step, as the swelling of polyvinylalcohol is increased, the coated layer of the tablet bursts and a drug in the tablet is released freely. In this case polyvinylalcohol in the tablet forms a matrix and the drug is trapped in the matrix and the matrix forms a gel that gradually erodes from its surface and accompanied with it the drug is gradually released.

As mentioned above, total release patterns of releasing a drug in the controlled release preparation of this invention show a two-phases pattern consisting of slow release rate in the initial phase and fast release rate in the last phase, sigmoidal pattern consisting of slow release rate in the initial phase and the last phase and fast release rate in the middle phase, or zero-order pattern with constant release rate.

In the controlled release preparation of this invention, by controlling the amount of polyvinylalcohol in an uncoated core-tablet, the amount (ratio) of a water-soluble polymer, the amount of one or more salts selected from a group consisting of trisodium citrate, sodium sulfate and sodium chloride which control the swelling of polyvinylalcohol, or the amount of a water-insoluble polymer and a water-soluble polymer and/or an enteric polymer and the amount of the membrane coated on, the release rate in the first step that the drug is released via pores, the burst time of the membrane and the release rate in the second step that the drug is released after the burst of the membrane and so on, are intentionally controllable and thereby preparations having many kinds of the release patterns as mentioned above can be prepared.

Consequently in the controlled release preparation of this invention, the release pattern can be optionally chosen according to the drug. Therefore, the controlled release preparation of this invention can become a controlled release preparation suitable for oral administration once or twice a day.

By doing the enteric coating on the above mentioned controlled release preparation, or by coating a mixture of a drug and a water-soluble polymer or a solid dispersion thereof on the above mentioned controlled release preparation or enteric coated tablet, to extend further the plasma level of the drug and maintain plasma level during the initial stage of administration is obtainable.

From these matters, it is possible to make the preparation of this invention into a preparation in consideration of circadianrhythm.

Further, because one embodiment of the preparation of this invention is a small sized tablet form, not only the adjustment of dose accorded with disease syndrome or age is easy but also it can be possible to take them once by filling them into a capsule (see the test examples 1 to 3 described later).

By illustrating the following test examples the effect of this invention is explained in detail. As drugs, emedastine difumarate, lomerizine hydrochloride, trazodone hydrochloride and nifedipine are used and evaluated.
Test 1(dissolution test)
(1) Sample
Tablets prepared by Examples 1 to 18, 20, 22 and 24(see table 1 to 4. Unit:mg)

TABLE 1

| component | 1 | 2 | 3 | 4 | 5 |
|---|---|---|---|---|---|
| uncoated core-tablet | | | | | |
| emedastine difumarate | 4 | 4 | 4 | 4 | 4 |
| HPC | 1 | 1 | 1 | 1 | 1 |
| polyvinylalcohol | 30 | 27.5 | 25 | 25 | 25 |
| trisodium citrate.2H$_2$O | 10 | 10 | 10 | 2 | 3 |
| lactose | 4 | 6.5 | 9 | 17 | 16 |
| light anhydrous silicic acid | 0.5 | 0.4 | 0.5 | 0.4 | 0.4 |
| magnesium stearate | 0.5 | 0.6 | 0.5 | 0.6 | 0.6 |
| subtotal | 50 | 50 | 50 | 50 | 50 |
| coating membrane | | | | | |
| ethylcellulose | 3.5 | 3.5 | 3.5 | 3.5 | 3.5 |
| HPMC | 1.5 | 1.5 | 1.5 | 1.5 | 1.5 |
| triethyl citrate | 1 | 1 | 1 | 1 | 1 |
| total | 56 | 56 | 56 | 56 | 56 |

TABLE 2

| component | 6 | 7 | 8 | 9 | 10 | 11 |
|---|---|---|---|---|---|---|
| uncoated core-tablet | | | | | | |
| emedastine difumarate | 4 | 4 | 4 | 4 | 4 | 4 |
| HPC | 1 | 1 | 1 | 1 | 1 | 5 |
| polyvinylalcohol | 30 | 30 | 30 | 30 | 30 | 30 |
| trisodium citrate.2H$_2$O | 10 | 10 | — | — | — | — |
| sodium chloride | — | — | 10 | 10 | — | — |
| sodium sulfate | — | — | — | — | 10 | 10 |
| lactose | 4 | 4 | 4 | 4 | 4 | — |
| light anhydrous silicic acid | 0.4 | 0.4 | 0.4 | 0.4 | 0.4 | 0.4 |
| magnesium stearate | 0.6 | 0.6 | 0.6 | 0.6 | 0.6 | 0.6 |
| subtotal | 50 | 50 | 50 | 50 | 50 | 50 |
| coating membrane | | | | | | |
| ethylcellulose | 3.5 | 4.1 | 3.5 | 4.1 | 3.5 | 3.5 |
| HPMC | — | — | 1.5 | 1.7 | 1.5 | 1.5 |
| HPC | 1.5 | 1.7 | — | — | — | — |
| triethyl citrate | 1 | 1.2 | 1 | 1.2 | 1 | 1 |
| total | 56 | 57 | 56 | 57 | 56 | 56 |

TABLE 3

| component | 12 | 13 | 14 | 15 | 16 | 17 |
|---|---|---|---|---|---|---|
| uncoated core-tablet | | | | | | |
| lomerizine hydrochloride | 5 | 5 | 5 | 5 | — | — |
| trazodone hydrochloride | — | — | — | — | 75 | 75 |
| HPC | 1 | 1 | 1 | 1 | 4 | 4 |
| polyvinylalcohol | 20 | 20 | 25 | 25 | 80 | 80 |
| sodium chloride | 20 | 20 | — | — | — | — |
| trisodium citrate.2H$_2$O | — | — | 15 | 15 | 40 | 40 |
| lactose | 3 | 3 | 3.2 | 3.2 | — | — |
| light anhydrous silicic acid | 0.3 | 0.3 | 0.4 | 0.4 | 1 | 1 |
| magnesium stearate | 0.7 | 0.7 | 0.4 | 0.4 | 2 | 2 |
| subtotal | 50 | 50 | 50 | 50 | 202 | 202 |

TABLE 3-continued

| | example number | | | | | |
|---|---|---|---|---|---|---|
| component | 12 | 13 | 14 | 15 | 16 | 17 |
| coating membrane | | | | | | |
| ethylcellulose | 3.4 | 4.5 | 3.4 | 4.6 | 6.3 | 10.2 |
| HPMC | 1.6 | 2.2 | 1.6 | 2.1 | 2.9 | 4.8 |
| triethyl citrate | 1 | 1.3 | 1 | 1.3 | 1.8 | 3 |
| total | 56 | 58 | 56 | 58 | 213 | 220 |

TABLE 4

| | example number | | | |
|---|---|---|---|---|
| component | 18 | 20 | 22 | 24 |
| uncoated core-tablet | | | | |
| nifedipine | 5 | 5 | 3.75 | 3.75 |
| HPMC | 7.5 | 7.5 | 5.63 | 5.65 |
| polyvinylalcohol | 40 | 40 | 40 | 25 |
| trisodium citrate.2H$_2$O | 6.7 | 6.7 | 6.7 | 6.7 |
| crystalline cellulose | — | — | — | 10 |
| light anhydrous silicic acid | 0.5 | 0.5 | 0.5 | 0.5 |
| magnesium stearate | 0.3 | 0.3 | 0.3 | 0.3 |
| subtotal | 60 | 60 | 56.88 | 51.9 |
| coating membrane | | | | |
| ethylcellulose | 3.1 | 2.9 | 2.65 | 2.4 |
| HPMC | 1.9 | 2.1 | 1.85 | — |
| HPMCP | — | — | — | 1.6 |
| triethyl citrate | — | — | — | 0.8 |
| HPMCP | — | 3 | 3 | — |
| nifedipine | — | — | 1.25 | 1.25 |
| HPMC | — | — | 1.87 | 1.9 |
| total | 65 | 68 | 67.5 | 59.85 |

(2) Test Method

This method was conducted according to the dissolution method No. 2 (paddle method) in JP. As a dissolution medium, 1st fluid or 2nd fluid of JP, or acetic acid-sodium acetate buffer solution (pH4.0) was used. The temperature of the dissolution medium was kept at 37° C. and the revolution was set at 50 rpm. The release rate of emedastine difumarate, trazodone hydrochloride or nifedipine was determined by measurement of absorbance at 280 nm, 312 nm, and 325 nm.

The release rate of lomerizine hydrochloride was determined by liquid chromatography (abbreviated to HPLC) on the following conditions.

Condition of HPLC:

Column: L-column TMODS [150 mm×4.6 mm; Chemicals Inspection & Testing Institute]

Mobile phase: a mixed solution of 3 parts of methanol and 1 part of aqueous 5W/V% sodium laurylsulfate solution adjusted pH to 2.5

Column temperature: 50° C.

Flow rate: 1.4 ml/min.

Detection: absorbance at UV225 nm (3) Test Result

The result (average of 3 to 6 samples) was shown in FIGS. 9 to 19.

Figure 9:
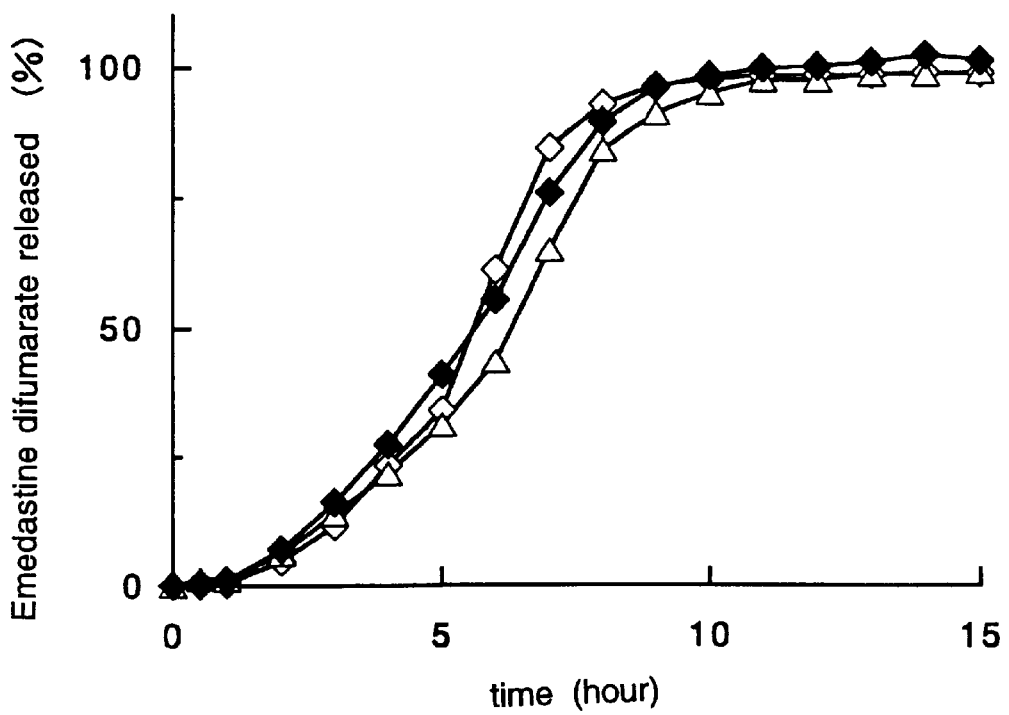
FIG. 9 shows the result of the dissolution test of emedastine difumarate from a tablet prepared by Example 1, and in FIG. 9, ◇ mark means a case in which as a dissolution medium were used 1st fluid (pH1.2) in the disintegration test described in Japanese Pharmacopeia 12th edition (published by Dai-ichi Hoki, 1991: abbreviated to JP), ◆ mark is in case of using acetic acid-sodium acetate buffer solution (pH4.0) in JP as a dissolution medium, and Δ mark is in case of using 2nd fluid (pH6.8) in the disintegration test in JP.

FIG. 9 shows the result on the effect of dissolution medium (pH) tested by using emedastine difumarate as a drug. As is clear from FIG. 9, in every dissolution medium, release of emedastine difumarate began from one hour, the membrane burst 5 hours later and thereafter the release rate became fast. The release rate was hardly effected by the dissolution medium.

Figure 10:
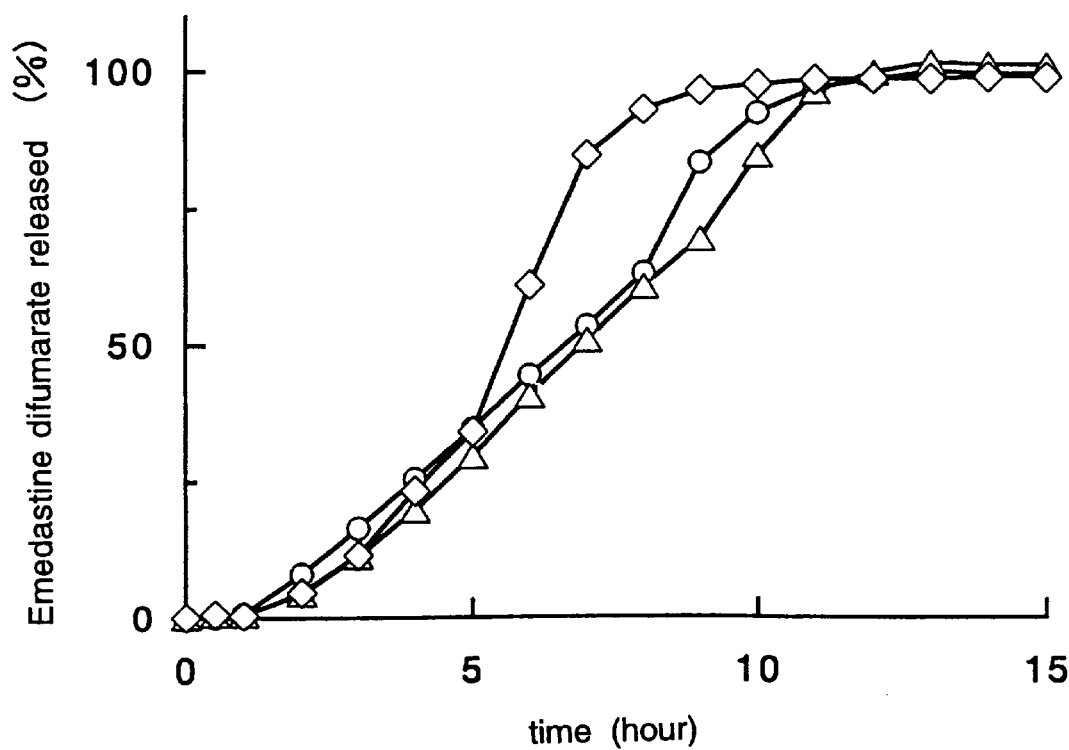
FIG. 10 shows the result of the dissolution test of emedastine difumarate from tablets prepared by Examples 1 to 3 (dissolution medium: 1st fluid (pH1.2) in the disintegration test in JP), ◇ mark is on a tablet of Example 1, ○ mark is on a tablet of Example 2, and Δ mark is on a tablet of Example 3.

FIG. 10 shows the effect of the amount of polyvinylalcohol in the uncoated core-tablet containing emedastine difumarate on the release rate. As is clear from FIG. 10, in proportion with increase of the amount of polyvinylalcohol, burst of the membrane began faster and the release rate was accelerated.

Figure 11:
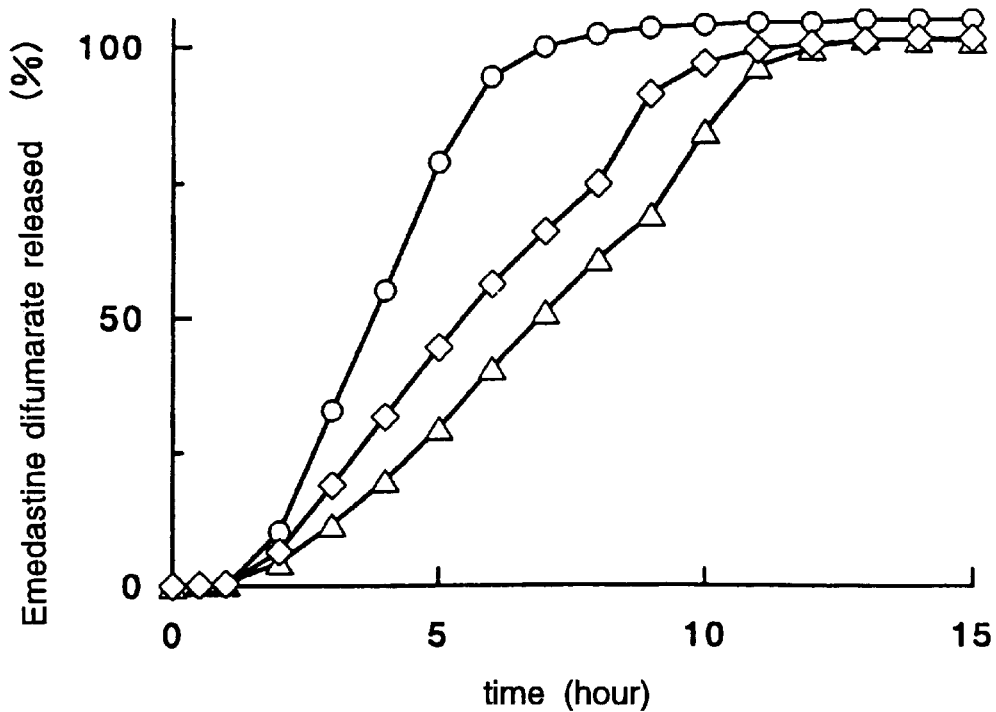
FIG. 11 shows the result of the dissolution test of emedastine difumarate from tablets prepared by Examples 3 to 5 (dissolution medium: 1st fluid (pH 1.2) in the disintegration test in JP), Δ mark is on a tablet of Example 3, ○ mark is on a tablet of Example 4 and ◇ mark is on a tablet of Example 5.

FIG. 11 shows the effect of the amount of a salt, trisodium citrate in the uncoated core-tablet containing emedastine difumarate on the release rate. As is clear from FIG. 11, with decrease of the amount of trisodium citrate, burst of the membrane began faster and the release rate was accelerated.

Figure 12:
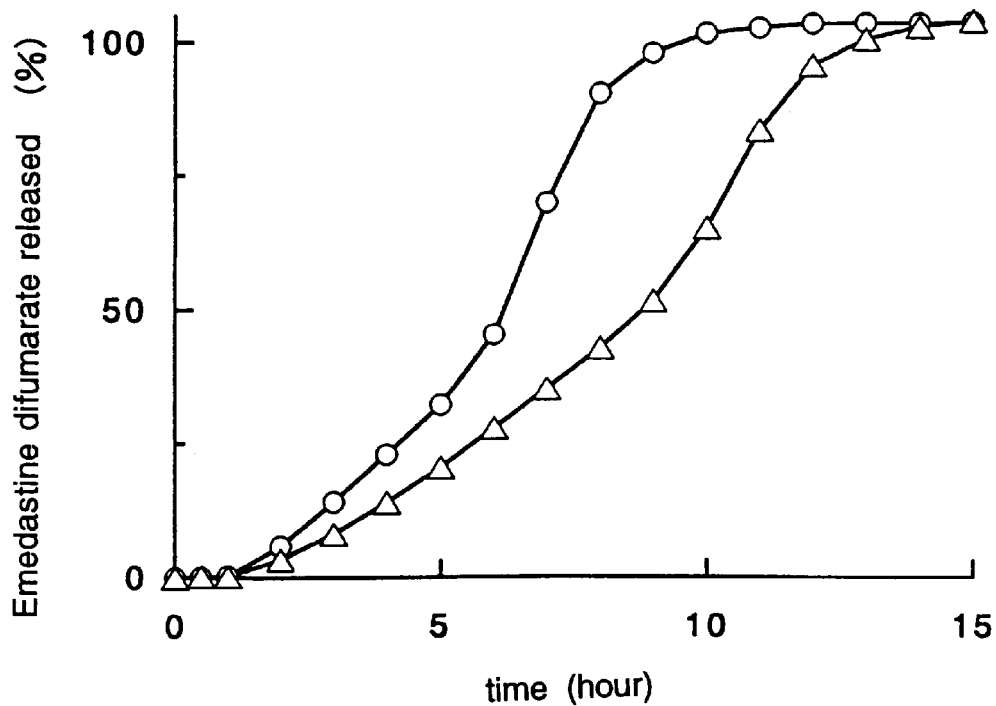
FIG. 12 shows the result of the dissolution test of emedastine difumarate from tablets prepared by Examples 6 and 7 (dissolution medium: 1 st fluid (pH1.2) in the disintegration test in JP), ○ mark is on a tablet of Example 6, and Δ mark is on a tablet of Example 7.
Figure 13:
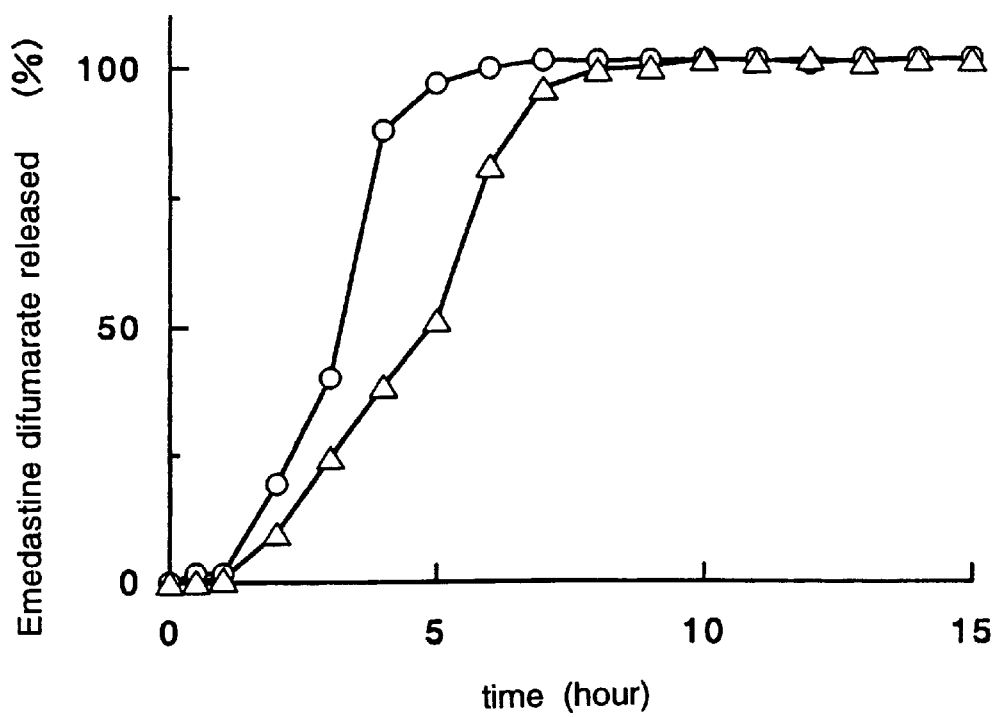
FIG. 13 shows the result of the dissolution test of emedastine difumarate from tablets prepared by Examples 8 and 9 (dissolution medium: 1st fluid (pH1.2) in the disintegration test in JP), ○ mark is on a tablet of Example 8 and Δ mark is on a tablet of Example 9.

FIGS. 12 and 13 show the result on the effect of the amount of the coated membrane of a water-soluble pore-forming membrane on the tablet containing emedastine difumarate on the release rate. As is clear from FIGS. 12 and 13, with increase of the amount of the coated membrane on the water-soluble pore-forming membrane, burst time of the membrane was prolonged and the release rate became slow.

Figure 14:
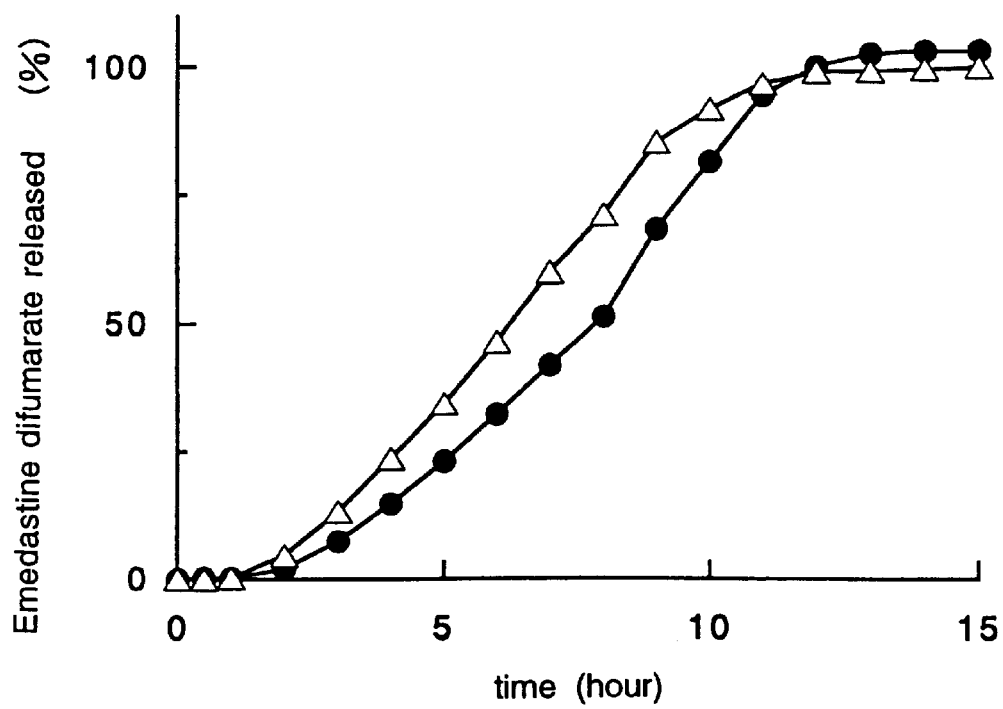
FIG. 14 shows the result of the dissolution test of emedastine difumarate from tablets prepared by Example 10 to 11 (dissolution medium: 1st fluid (pH1.2) in the disintegration test in JP), Δ mark is on a tablet of Example 10, and ● mark is on a tablet of Example 11.

FIG. 14 shows the effect on the release rate when a water-soluble polymer was added or not added in the uncoated core-tablet containg emedastine difumarate as a drug. As is clear from FIG. 14, with addition of a water-soluble polymer, the release rate became slow.

Figure 15:
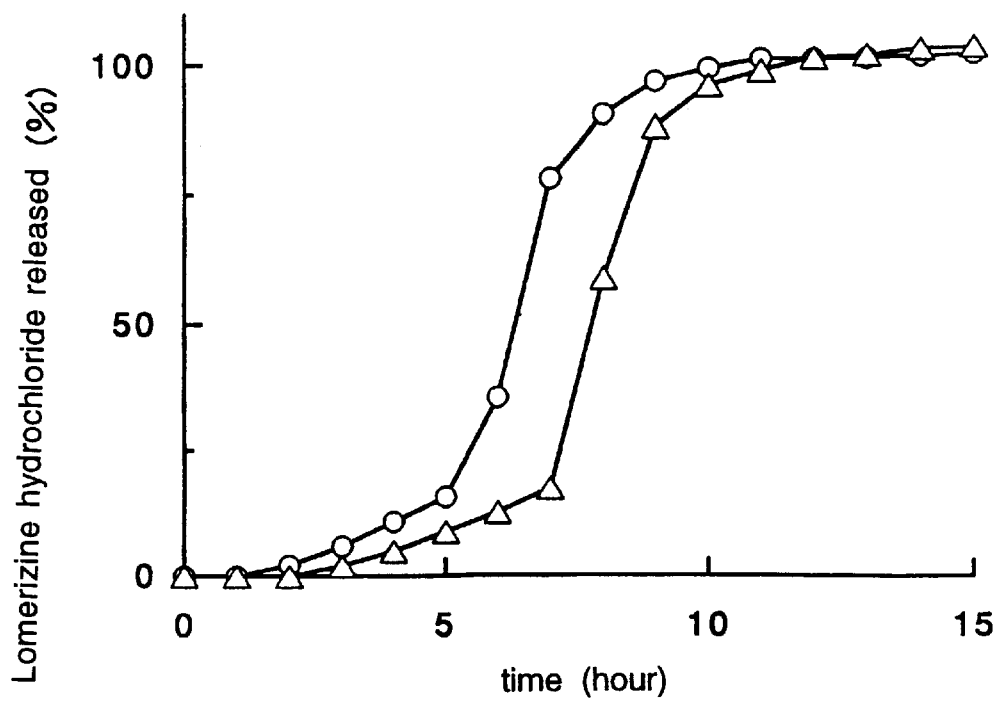
FIG. 15 shows the result of the dissolution test of lomerizine hydrochloride from tablets prepared by Example 12 to 13 (dissolution medium: 1st fluid (pH1.2) in the disintegration test in JP), ○ mark is on a tablet of Example 12 and Δ mark is on a tablet of Example 13.
Figure 16:
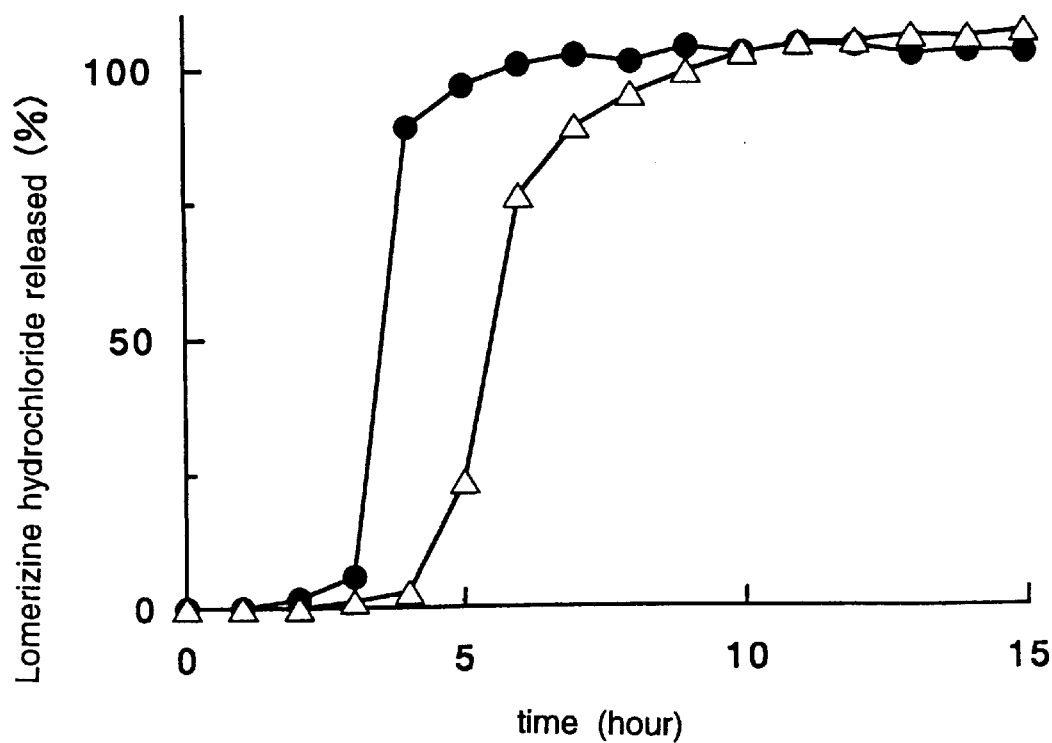
FIG. 16 shows the result of the dissolution test of lomerizine hydrochloride from tablets prepared by Example 14 to 15 (dissolution medium: 1st fluid (pH1.2) in the disintegration test in JP), ● mark is on a tablet of Example 14, Δ mark is a tablet of Example 15.

FIGS. 15 and 16 show the effect of the amount of the water-soluble pore-forming membrane on the tablet containing lomerizine hydrochloride on the release rate. As is clear from FIGS. 15 and 16, in proportion with increase of the amount of the water-soluble pore-forming membrane on the tablet, burst time of the membrane was prolonged and the release rate became slow.

Figure 17:
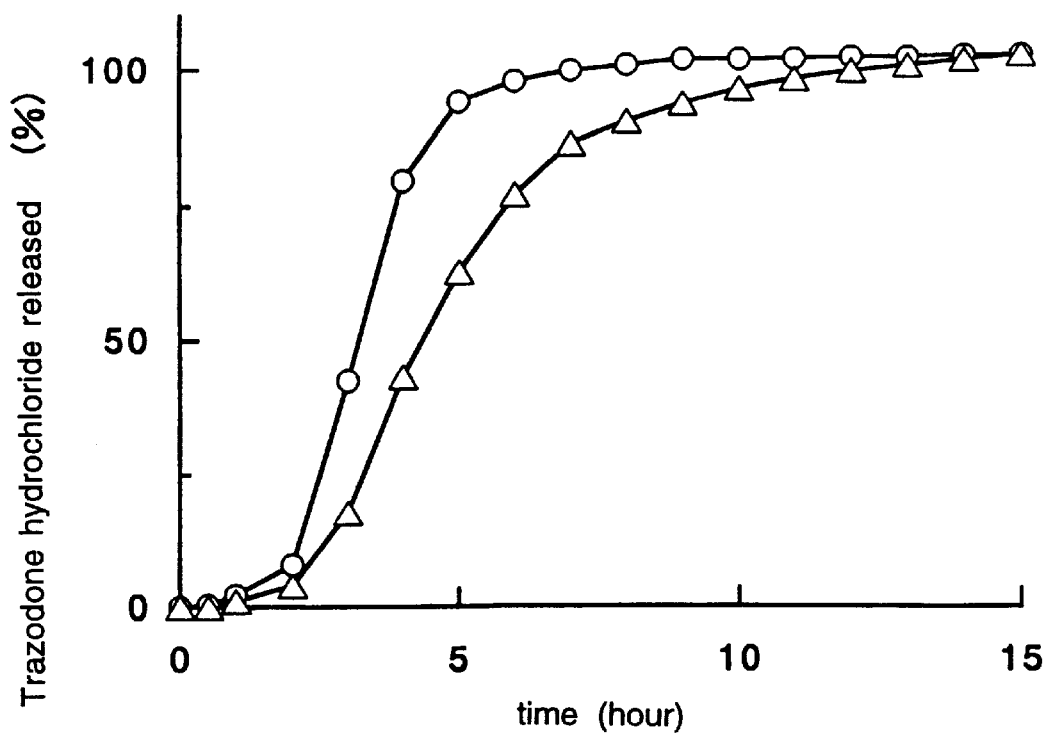
FIG. 17 shows the result of the dissolution of trazodone hydrochloride from tablets prepared by Example 16 and 17 (dissolution medium: 1st fluid (pH1.2) in the disintegration test in JP), ○ mark is on a tablet of Example 16 and Δ mark is on a tablet of Example 17.

FIG. 17 shows the effect of the amount of the water-soluble pore-forming membrane on the tablet (8 mm in diameter) containing trazodone hydrochloride on the release rate. As is clear from FIG. 17, in proportion with increase of the amount of the water-soluble pore-forming membrane on the tablet even in using the tablet with larger diameter, burst time of the membrane was prolonged and the release rate became slow.

Figure 18:
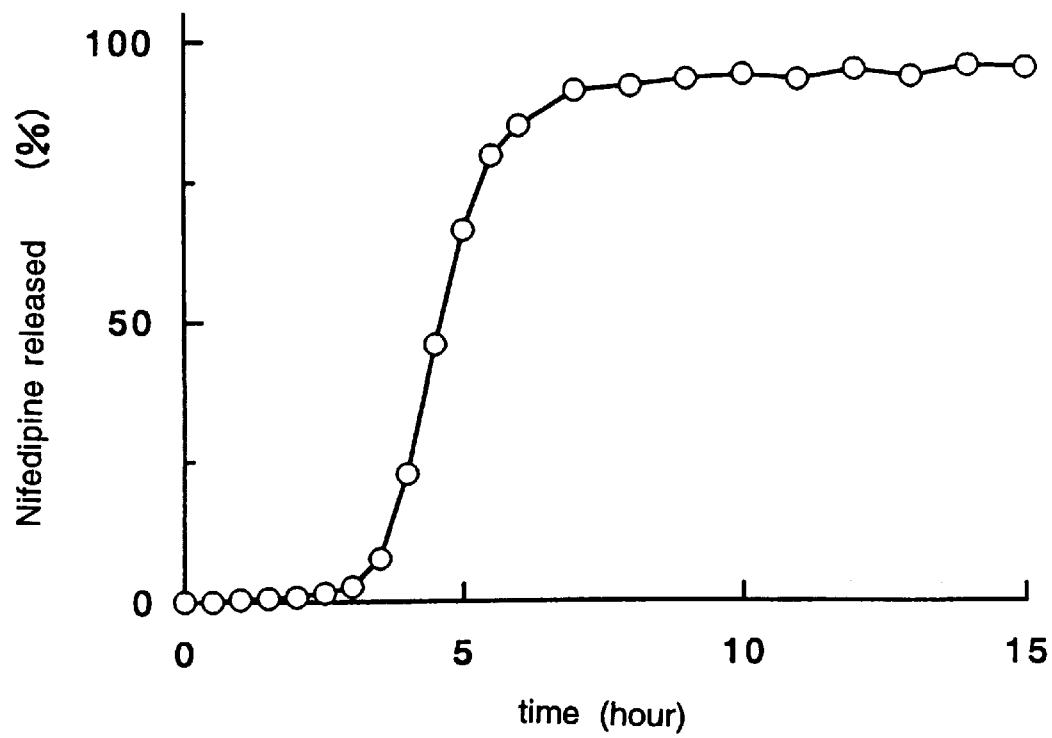
FIG. 18 shows the result of the dissolution of nifedipine from a tablet prepared by Example 18 (dissolution medium:2nd fluid (pH6.8) in disintegration test in JP.

FIG. 18 shows the result of the effect of the tablet coated with the water-soluble pore-forming membrane (Example 18) containing nifedipine on the release rate. As is clear from FIG. 18, release of nifedipine from the controlled release tablet (Example 18) began from three hours, and at three and a half hours the membrane burst, followed by rapid release of nifedipine.

Figure 19:
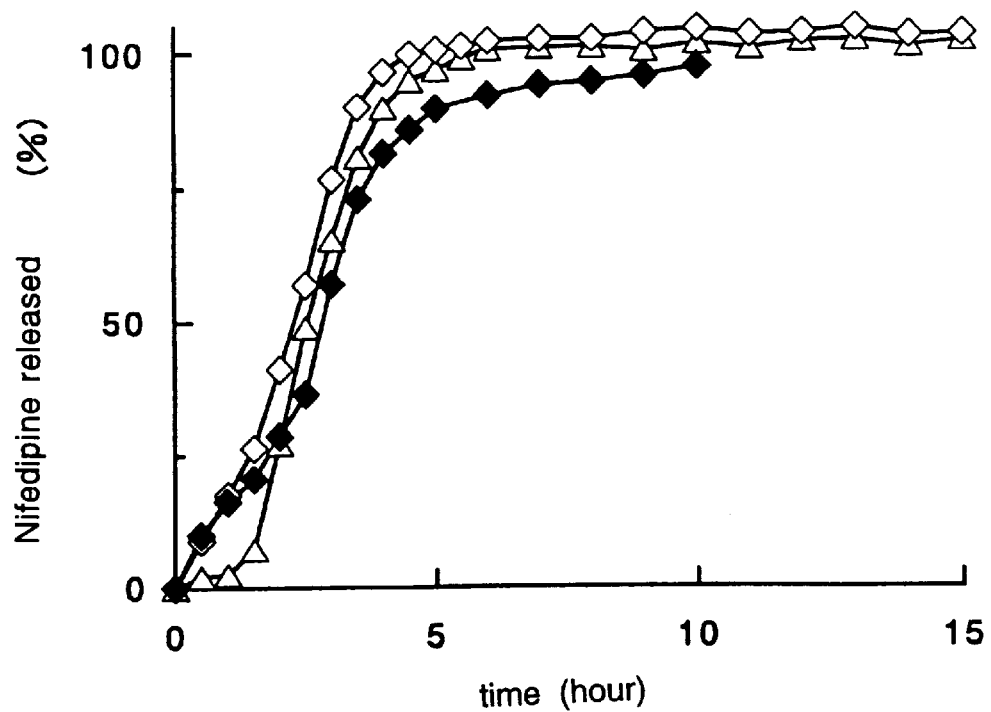
FIG. 19 shows the result of the dissolution of nifedipine from tablets prepared by Examples 20, 22 and 24 (dissolution medium:2nd fluid (pH6.8) in the disintegration test in JP), Δ mark is on a tablet of Example 20, ◇ mark is on a tablet of Example 22 and ♦ mark is on a tablet of Example 24.

FIG. 19 shows the result of the effect of the tablet coated with the water-soluble pore-forming membrane and further coated with the enteric membrane (Example 20) containing nifedipine, the tablet coated with the water-soluble pore-forming membrane, with the enteric membrane and further coated with a solid dispersion membrane (Example 22), and the tablet coated with the enteric pore-forming membrane and further coated with a solid dispersion membrane (Example 24) (each tablet containing nifedipine) [dissolution medium: 2nd fluid (pH6.8) of disintegration test described in JP]. Release of nifedipine from the controlled release tablet of Example 20 in 2nd fluid (pH6.8) began from one hour and the membrane burst at two hours, followed by rapid release of nifedipine. In 1st fluid (pH1.2), release of nifedipine was not detected until 10 hours. Release of nifedipine from the controlled release tablet of Example 22 began immediately, and the membrane burst at two hours, followed by rapid release of nifedipine. Release of nifedipine from the controlled release tablet of Example 24 began immediately and the membrane burst at three hours, followed by rapid release of nifedipine. Either on the controlled release tablet of Example 22 or Example 24, in 1st fluid (pH1.2), only nifedipine in a solid dispersion membrane-coated as the most outlayer was gradually released and burst of the membrane could not be found until 10 hours.

Test 2 (measurement of urinary excretion rate)

Absorption test of the preparation of this invention was evaluated by using urinary excretion rate of the main metabolite of nifedipine, 2,6-dimethyl-4- (2-nitrophenyl)-3, 5-pyridine carboxylic acid monomethylester (hereinafter abbreviated as the main metabolite) as indicator. The concentration in urea of the main metabolite of nifedipine was determined by HPLC on the following conditions.

Condition of HPLC:

Column:Nova-PakTMC 18[150 mm×3.9 mm; Waters]

Mobile phase: a mixed solution of 5 parts of acetic acid(0.05M) and 1 part of acetonitrile Column temperature: 25° C.

Flow rate: 1.0 ml/min.

Detection method: absorbance at UV 290 nm (1) Sample

Capsules of Example 19, Example 21, Example 23 and Example 25 and a tablet of Comparative example 1

(2) Test Method

Each sample (containing 20 mg of nifedipine) was orally administered to 3 to 4 normal adult volunteers 30 minutes after breakfast and urine samples were collected between 0 to 1 hr, 1 to 2 hr, 2 to 4 hr, 4 to 6 hr, 6 to 8 hr, 8 to 10 hr, 10 to 12 hr, 12 to 15 hr, 15 to 22 hr and 22 to 24 hr. In addition to that, in cases of taking the capsule of Examples 21, 23 and 25, urine samples were collected between 24 to 27 hr, 27 to 30 hr and 30 to 33 hr and the concentration of the main metabolite of nifedipine was measured by HPLC and the urinary excretion rate at each time was calculated.

(3) Test Result

Figure 20:
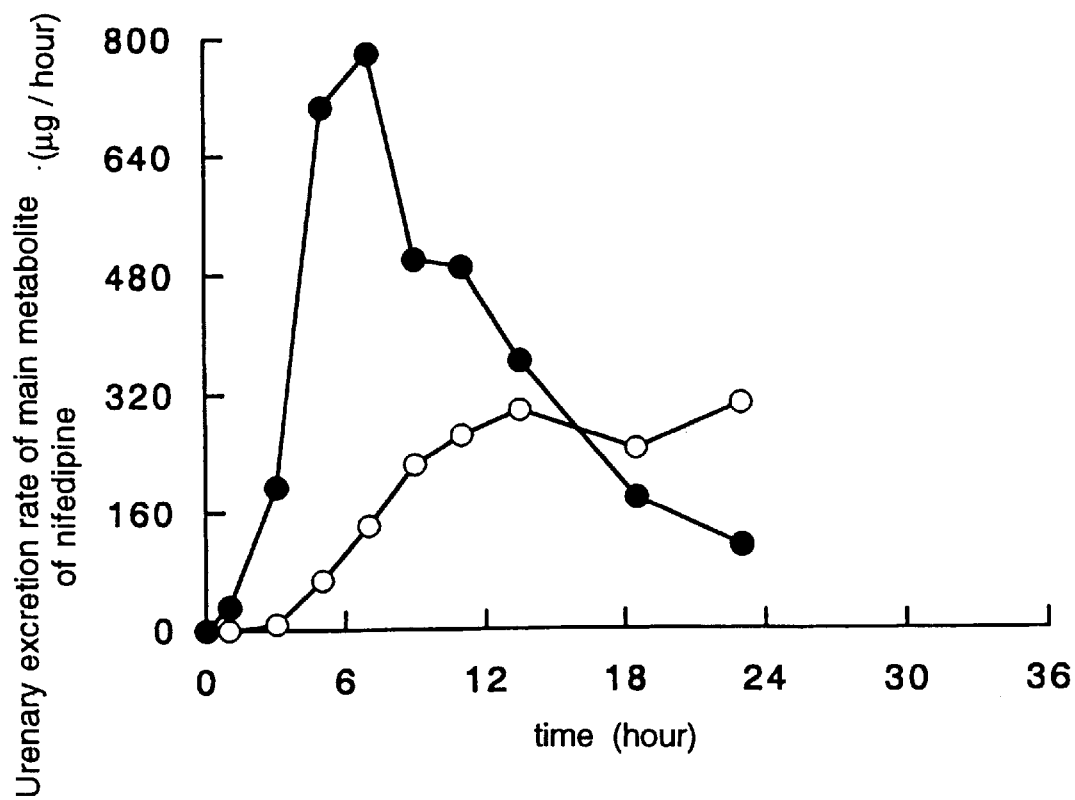
FIG. 20 shows a graph on a change of the urinary excretion rate of the main metabolite of nifedipine with the lapse of time after oral administration of a capsule of Example 19 and a tablet of Comparative example 1 to normal adult volunteers. ○ mark is on a capsule of Example 19 and ● mark is on a tablet of Comparative example 1.

When a capsule of Example 19 in which four tablets coated with the water-soluble pore-forming membrane (Example18) were filled and a tablet of Comparative example 1, each containing nifedipine, were administered, comparative data of the urinary excretion rate of the main metabolite was shown in FIG. 20. As is clear from FIG. 20, the urinary excretion rate in case of administration of the controlled release preparation of this invention (capsules) was longer sustained in comparison with that in case of administration of a u tablet of Comparative example 1 (controlled release preparation).

Figure 21:
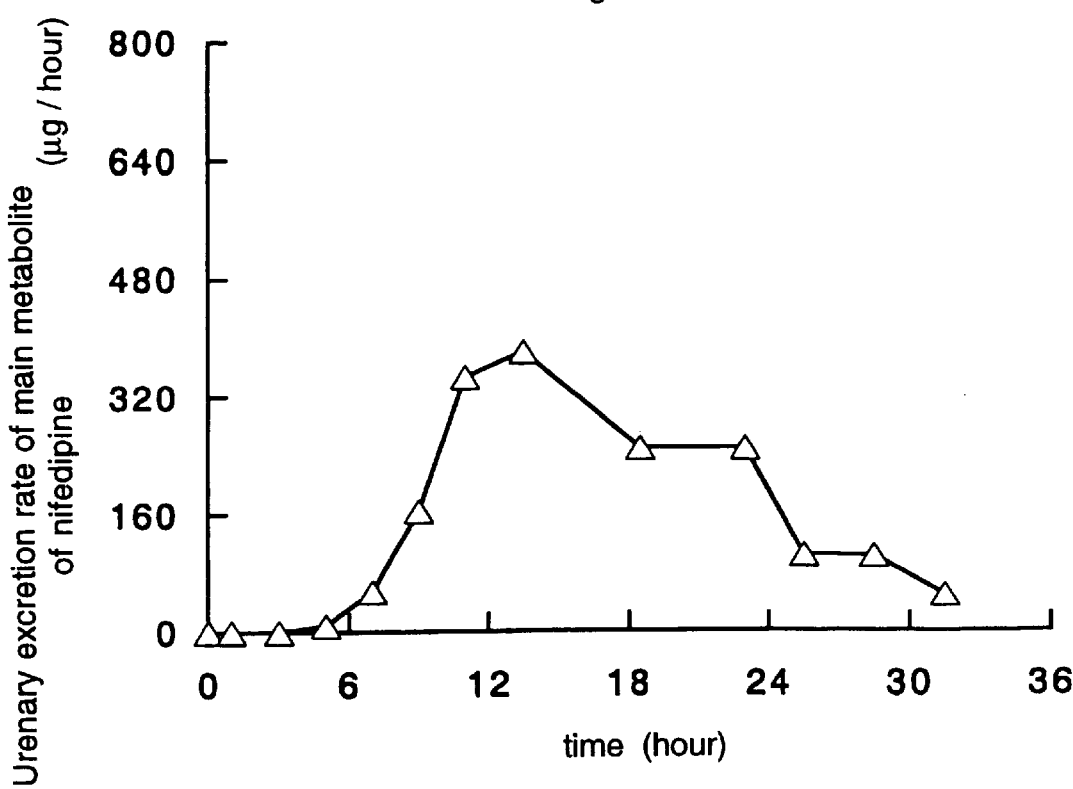
FIG. 21 shows a change of the urinary excretion rate of the main metabolite of nifedipine with the lapse of time after oral administration of a capsule of Example 21 to normal adult volunteers.
Figure 22:
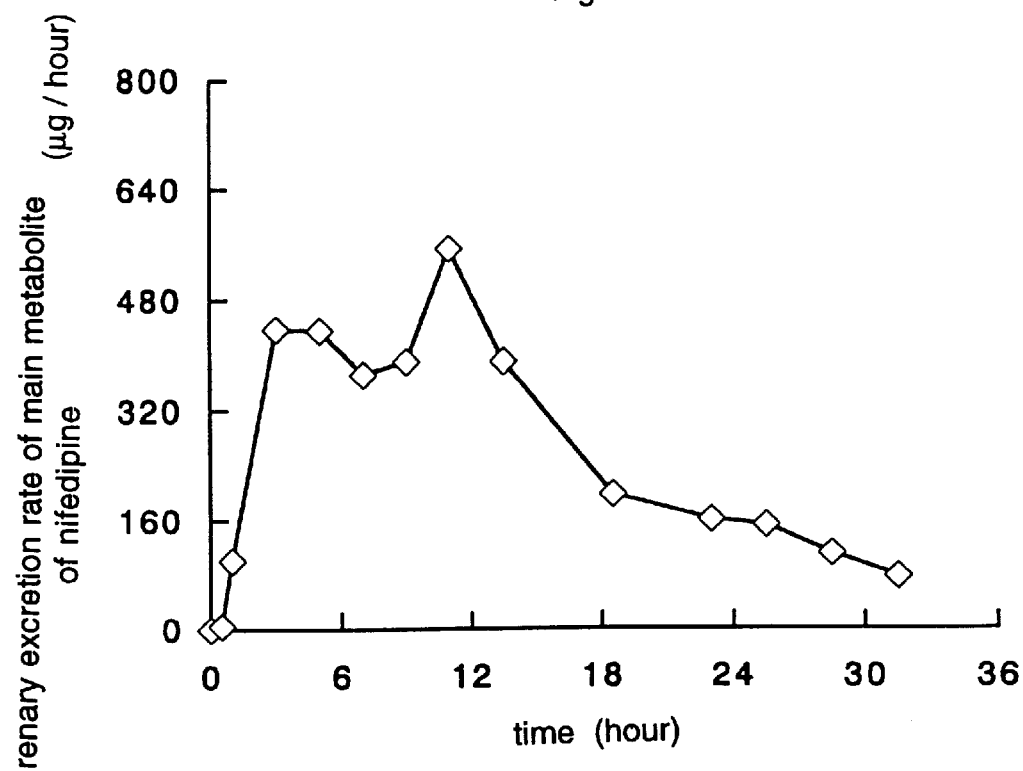
FIG. 22 shows a change of the urinary excretion rate of the main metabolite of nifedipine with the lapse of time after oral administration of a capsule of Example 23 to normal adult volunteers.
Figure 23:
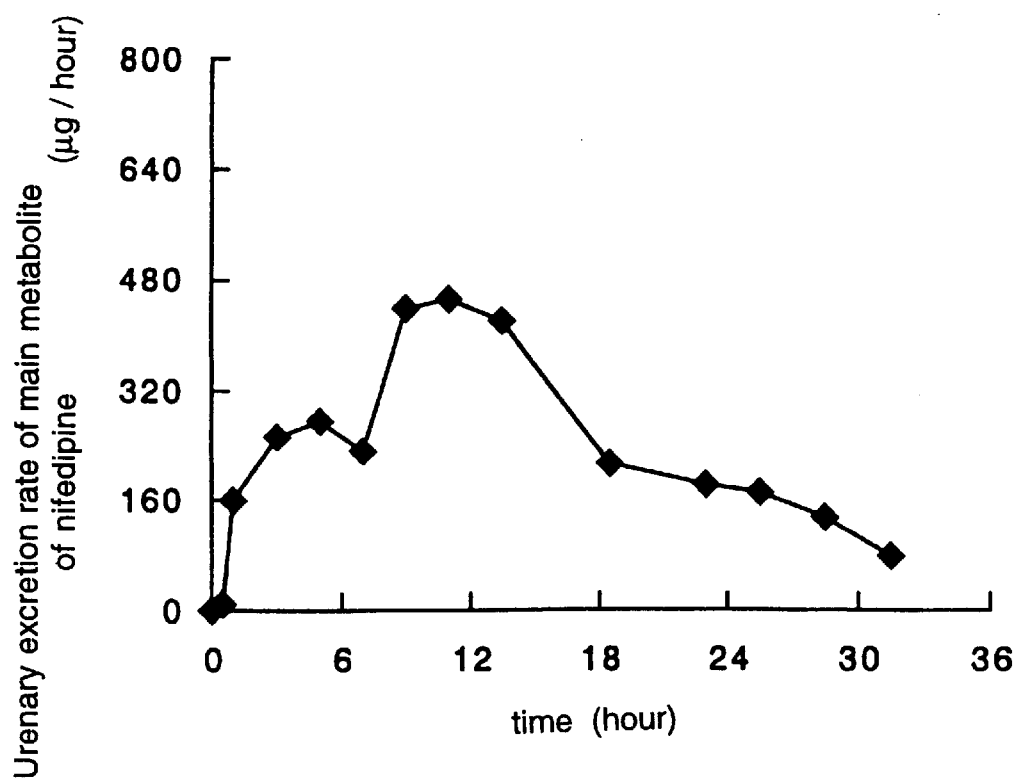
FIG. 23 shows a change of the urinary excretion rate of the main metabolite nifedipine with the lapse of time after oral administration of a capsule of Example 25 to normal adult volunteers.

Further, a capsule of Example 21 in which four tablets coated with the water-soluble pore-forming membrane and further coated with the enteric membrane (Example 20) were filled, a capsule of Example 23 in which four tablets coated with the water-soluble pore-forming membrane and further coated with the solid dispersion membrane (Example 22) were filled and a capsule of Example 25 in which four tablets coated with the enteric pore-forming membrane and further coated with the solid dispersion membrane (Example 24) were filled, were administered to normal adult volunteers and in that case the urinary excretion rate of the main metabolite was measured and the results are shown in FIGS. 21 to 23. As is clear from FIGS. 21 to 23, the urinary excretion rate was longer sustained when the controlled release preparation of this invention which was coated with enteric membrane on the surface of the water-soluble pore-forming membrane coated tablet was administered in the form of capsule.

And in case of administration of the preparation of this invention which was coated with the solid dispersion membrane, on the water-soluble pore-forming membrane coated tablet or the enteric membrane coated tablet, in form of a filled capsule, the urinary excretion rate of the initial stage was secured and sustained for long hours.

Test 3 (measurement of plasma level)

The plasma level of nifedipine was determined by gas chromatography (abbreviated to GC) on following conditions.

Condition of GC

Detector: electron capture detector

Column: 3%OV-17 (3 mm×3.1 m; GL Science Inc.)

Column temperature: 270° C.

(1) Sample

A capsule of Example 19

(2) Test Method

Six normal adult volunteers took breakfast and 30 minutes later the sample was orally administered. In definite times after administration (2, 4, 8, 10, 12, 15, 24, 28, 32, 36, 48 hr) the blood was taken and centrifuged to obtain plasma. The plasma level of nifedipine which took at each hours was determined by GC.

(3) Result of Test

Figure 24:
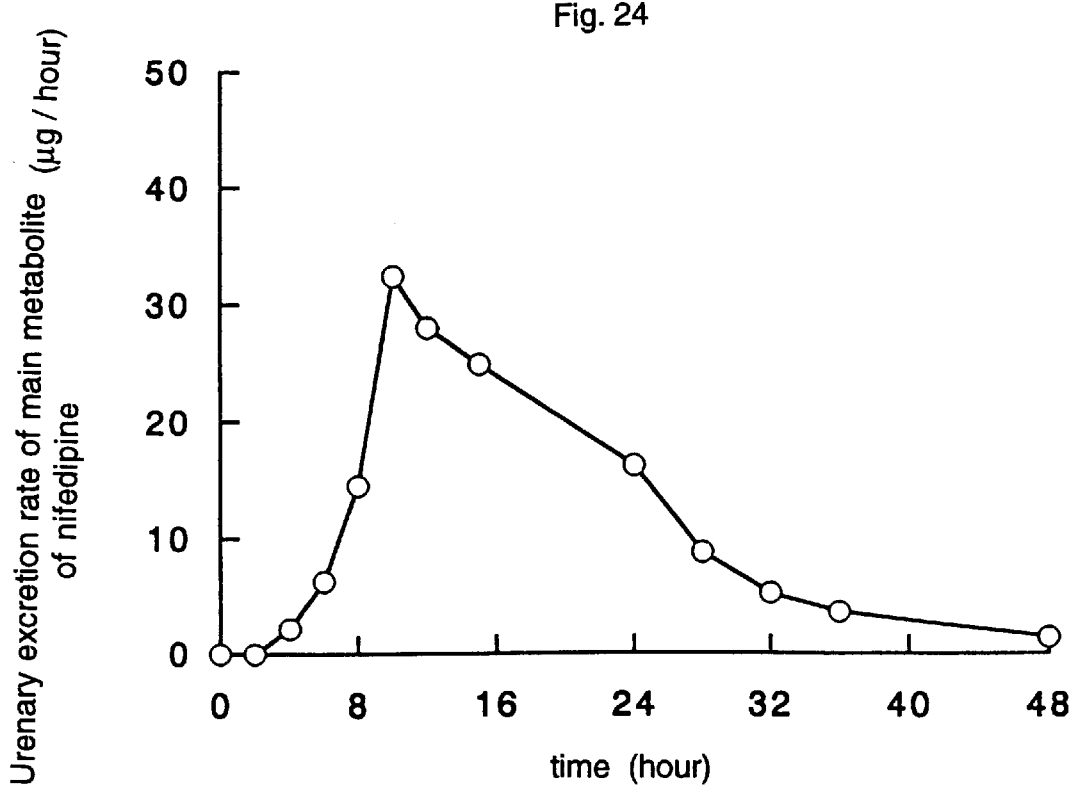
FIG. 24 shows a change of the plasma level of nifedipine with the lapse of time after oral administration of a capsule of Example 19 to normal adult volunteers.

Change with the lapse of time of the plasma level of nifedipine (average amount) when the water-soluble pore-forming membrane coated tablet of this invention was administered to normal adult volunteers, was shown in FIG. 24. As is clear from FIG. 24, when the controlled release preparation of this invention was orally administered to normal adult volunteers, the high plasma level of nifedipine lasted for long hours. Therefore, the preparation of this invention has advantages in the oral absorption and the lasting of the high plasma level on a hardly water-soluble drug, and is useful for dosage form once or twice a day.

Following examples with a comparative example are illustrated to explain the present invention.

EXAMPLE 1

A mixture of emedastine difumarate (98 g) (see Japanese Patent Publication No. 24821/1990), polyvinylalcohol (trade name: Kuraray Poval PVA-CSTS; Kuraray Co., Ltd.) (734.7 g), trisodium citrate dihydrate (244.9 g) (sieved with Sieve No. 100) and lactose (98 g) was admixed in the fuluidized bed granulator, and to the mixture a solution of hydroxypropylcellulose (trade name: Nisso HPC; Nippon Soda Co., Ltd.) (24.4 g) in water (463 g) was sprayed as a binder and then the mixture was dried, and sieved with Sieve No. 18 to produce granules containing the drug. To the granules (1,114 g) magnesium stearate (11.3 g) and light silicic acid anhydride (11.3 g) were admixed, and the mixture was compressed into tablets each weighing 50 mg by using a rotary tableting machine with a punch 5 mm in diameter to produce uncoated core-tablets 753 g (about 15,100 tablets).

Next, ethyl cellulose (1 weight part) (trade name: Ethocel standard-10; Dow Chemical Co., Ltd.), hydroxypropylmethylcellulose (0.43 weight part) (trade name: TC-5E; Shin-Etsu Chemical Co., Ltd.), and triethyl citrate (0.29 weight part) (trade name: Citroflex 2; Pfizer Co., Ltd.) were dissolved in a mixture of water and ethanol [1:4 (weight ratio) so that the concentration of ethylcellulose and hydroxypropylmethylcellulose amounted to 5 weight percent. The resulting solution was used as a water-soluble pore-forming membrane solution.

The above uncoated core-tablets (350 g) (about 7,000 tablets) was put in the tablet coating machine (trade name:

Hi-Coater. HCT-MINI; Freund Ind. Co., Ltd.) and then said membrane solution was sprayed on the tablets in the coating machine and the tablets were dried to produce the coated tablets each weighing 56 mg. The controlled release preparation of this invention thus obtained contains emedastine difumarate 4 mg/tablet.

EXAMPLE 2

A mixture of emedastine difumarate (72 g), polyvinylalcohol (495 g) (trade name: Kuraray Poval PVA-CSTS; Kuraray Co., Ltd.), trisodium citrate dihydrate (180 g) (sieved with Sieve No. 100) and lactose (117 g) was admixed in the fluidized bed granulator, and to the mixture a solution of hydroxypropylcellulose (trade name: Nisso HPC; Nippon Soda Co., Ltd.) (18 g) in water (342 g) was sprayed as a binder and then the mixture was dried and sieved with Sieve No. 18 to make granules containing the drug. To these granules (855 g), magnesium stearate (10.5 g) and light anhydrous silicic acid (7 g) were admixed and the mixture was compressed by using a rotary tableting machine with a punch 5 mm in diameter to produce uncoated core-tablets (737 g) (about 14,700 tablets).

Next, in the same manner as in Example 1, on the uncoated core-tablets (350 g) (about 7,000 tablets), a water-soluble pore-forming membrane solution was sprayed and the tablets were dried to produce coated tablets each weighing 56 mg. The controlled release preparation of this invention thus obtained contains emedastine difumarate 4 mg per tablet.

EXAMPLE 3

A mixture of emedastine difumarate (152 g), polyvinylalcohol (950 g) (trade name: Kuraray Poval PVA-CSTS, Kuraray Co., Ltd.), trisodium citrate dihydrate (380 g) (sieved with Sieve No. 100) and lactose (342 g) was admixed in the fluidized bed granulator, and to the mixture a solution of hydroxypropylcellulose (38 g) (trade name: Nisso HPC; Nippon Soda Co., Ltd.) in water (722 g) was sprayed as a binder, and the mixture was dried and sieved with Sieve No. 18 to produce granules containing the drug. To the granules (1,800 g) magnesium stearate (18.4 g) and light anhydrous silicic acid (18.4 g) were admixed and the mixture was compressed by using a rotary tableting machine with a punch 5 mm in diameter to produce uncoated core-tablets (1,680 g) each weighing 50 mg (about 33,600 tablets).

Next, in the same manner as in Example 1, a water-soluble pore-forming membrane solution was sprayed on the uncoated core-tablets (350 g) (about 7,000 tablets) and the tablets were dried to produce coated tablets each weighing 56 mg. The controlled release preparation of this invention thus prepared contains emedastine difumarate 4 mg per tablet.

EXAMPLE 4

A mixture of emedastine difumarate (72 g), polyvinylalcohol (450 g) (trade name: Kuraray Poval PVA-CSTS; Kuraray Co., Ltd.), trisodium citrate dihydrate (36 g) (sieved with Sieve No. 100) and lactose (306 g) was admixed in the fuluidized bed granulator, and to the mixture a solution of hydroxypropylcellulose (18 g) (trade name: Nisso HPC; Nippon Soda Co., Ltd.) in water (342 g) was sprayed as a binder and the mixture was dried and sieved with Sieve No. 18 to give granules. To the granules (855 g) magnesium stearate (10.5 g) and light anhydrous silicic acid (7 g) were admixed and the mixture was compressed by using a rotary tableting machine with a punch 5 mm in diameter to produce uncoated core-tablets (720 g) (about 14,400 tablets) each weighing 50 mg.

Next, in the same manner as in Example 1, a water-soluble pore-forming membrane solution was sprayed on the uncoated core-tablets (350 g) (about 7,000 tablets) and the tablets were dried to produce coated tablets each weighing 56 mg. The controlled release preparation of this invention thus prepared contains emedastine difumarate 4 mg per tablet.

EXAMPLE 5

A mixture of emedastine difumarate (72 g), polyvinylalcohol (450 g) (trade name: Kuraray Poval PVA-CSTS; Kuraray Co., Ltd.), trisodium citrate dihydrate (54 g) (sieved with Sieve No. 100) and lactose (288 g) was admixed in the fluidized bed granulator and to the mixture a solution of hydroxypropylcellulose (18 g) (trade name: Nisso HPC; Nippon Soda Co., Ltd.) in water (342 g) was sprayed as a binder, and the mixture was dried and sieved with Sieve No. 18 to give granules. To the granules (855 g) magnesium stearate (10.5g) and light anhydrous silicic acid (7 g) were admixed and the mixture was compressed by using a rotary tableting machine with a punch 5 mm in diameter to produce uncoated core-tablets (740 g) (about 14,800 tablets) each weighing 50 mg.

Next, in the same manner as in Example 1, a water-soluble pore-forming membrane solution was sprayed on the uncoated core-tablets (350 g) (about 7,000 tablets) and the tablets were dried to produce coated tablets each weighing 56 mg. The controlled release preparation of this invention thus obtained contains emedastine difumarate 4 mg per tablet.

EXAMPLE 6

A mixture of emedastine difumarate (72 g), polyvinylalcohol (540 g) (trade name: Kuraray Poval PVA-CSTS; Kuraray Co., Ltd.), trisodium citrate dihydrate (180 g) (sieved by Sieve No. 100) and lactose (72 g) was admixed in the fluidized bed granulator, and to the mixture a solution of hydroxypropylcellulose (18 g) (trade name: Nisso HPC; Nippon Soda Co., Ltd.) in water (342 g) was sprayed as a binder, and the mixture was dried and sieved with Sieve No. 18 to produce granules. To the granules (860 g), magnesium stearate (10.5g) and light anhydrous silicic acid (7 g) were admixed and the mixture was compressed by using a rotary tableting machine with a punch 5 mm in diameter to produce uncoated core-tablets 708 g (14,200 tablets) each weighing 50 mg per tablet.

Next, ethylcellulose (1 weight part) (trade name: Ethocel standard -10, Dow Chemical Co., Ltd.), hydroxypropylcellulose (0.43 weight part) (trade name: Nisso HPC; Nippon Soda Co., Ltd.) and triethyl citrate (0.29 weight part) (trade name: Citroflex 2; Pfizer Co., Ltd.) were dissolved in ethanol so that the concentration of ethylcellulose and hydroxypropylcellulose amounted to 5 weight percent. This solution was used as a water-soluble pore-forming membrane solution.

The above uncoated core-tablets (350 g) (about 7,000 tablets) were put in the tablet coating machine (trade name: Hi-coater. HCT-MINI; Freund Ind. Co., Ltd.) and on the tablets the water-soluble pore-forming membrane solution was sprayed and the tablets were dried to produce the coated tablets each weighing 56 mg. The controlled release preparation of this invention thus prepared contains emedastine difumarate 4 mg per tablet.

EXAMPLE 7

In the same manner as in Example 6, the mixture containing emedastine difumarate was compressed by using a punch 5 mm in diameter, to produce uncoated core-tablets (708 g) (about 14,200 tablets) each weighing 50 mg.

Next, on the uncoated core-tablets (350 g) (about 7,000 tablets) in the same manner as in Example 6 except for increasing the coating amount 1 mg per tablet, a water-soluble pore-forming membrane solution was sprayed and the tablets were dried to produce tablets each weighing 57 mg. The controlled release preparation of the present invention thus prepared contains emedastine difumarate 4 mg per tablet.

EXAMPLE 8

A mixture of emedastine difumarate (72 g), polyvinylalcohol (540 g) (trade name: Kuraray Poval PVA-CS; Kuraray, sieved by Sieve No. 100), sodium chloride (180 g) (sieved by Sieve No. 100), and lactose (72 g) was admixed in the fluidized bed granulator, and to the mixture a solution of hydroxypropylcellulose (18 g) (trade name: Nisso HPC, Nippon Soda Co., Ltd.) in water (342 g) was sprayed as a binder, and the mixture was dried and sieved by Sieve No. 18 to produce granules. To the granules (850 g) magnesium stearate (10.4 g) and light anhydrous silicic acid (7 g) were admixed, and the mixture was compressed by using a rotary tableting machine with a punch 5 mm in diameter to produce uncoated core-tablets (755 g) (about 15,100 tablets) each weighing 50 mg.

Next, in the same manner as in Example 1, a water-soluble pore-forming membrane solution was sprayed on the uncoated core-tablets (350 g) (about 7,000 tablets) and the tablets were dried to produce each weighing 56 mg. The controlled release preparation of this invention thus prepared contains emedastine difumarate 4 mg per tablet.

EXAMPLE 9

In the same manner as in Example 8, the mixture containing emedastine difumarate was compressed by using a rotary tableting machine with a punch 5 mm in diameter to produce uncoated core-tablets (755 g) (about 15,100 tablets) each weighing 50 mg.

Next, in the same manner as in Example 1 except for increasing the coating amount 1 mg per tablets, a water-soluble pore-forming membrane solution was sprayed on the tablets 350 g (about 7,000 tablets), and the tablets were dried to produce weighing 57 mg per tablet. The controlled release preparation of this invention thus prepared contains emedastine difumarate 4 mg per tablet.

EXAMPLE 10

A mixture of emedastine difumarate (72 g), polyvinylalcohol (540 g) (trade name: Kuraray Poval PVA-CSTS; Kuraray Co., Ltd.), anhydrous sodium sulfate (180 g) (sieved with Sieve No. 100) and lactose (72 g) was admixed in the fluidized bed granulator, and to the mixture a solution hydroxypropylcellulose (18 g) (trade name: Nisso HPC; Nippon Soda Co., Ltd.) in ethanol (342 g) was sprayed as a binder, and the mixture was dried and sieved with Sieve No. 18 to produce granules. To the granules (850 g) magnesium stearate (10.4 g) and light anhydrous silicic acid (7 g) were admixed and the mixture was compressed by using a rotary tableting machine with a punch 5 mm in diameter to produce uncoated core-tablets (770 g) (15,400 tablets) each weighing 50 mg.

Next, in the same manner as in Example 1, on the uncoated core-tablets (350 g) (about 7,000 tablets) a water-soluble pore-forming membrane solution was sprayed and the tablets were dried to produce tablets each weighing 56 mg. The controlled release preparation of the invention thus prepared contains emedastine difumarate 4 mg per tablet.

EXAMPLE 11

A mixture of emedastine difumarate (72 g), polyvinylalcohol (540 g) (trade name: Kuraray Poval PVA-CSTS; Kuraray Co., Ltd.), anhydrous sodium sulfate (180 g) (sieved with Sieve No. 100) and hydroxypropylcellulose (72 g) (Nisso HPC; Nippon Soda Co., Ltd.) was admixed in the fluidized bed granulator, and to the mixture a solution of hydroxypropylcellulose (18 g) in ethanol (342 g) was sprayed as a binder, and the mixture was dried and sieved with Sieve No. 18 to give granules. To the granules (850 g), magnesium stearate (10.4 g) and light anhydrous silicic acid (7 g) were admixed and the mixture was compressed by using a rotary tableting machine with a punch 5 mm in diameter to produce uncoated core-tablets (760 g) (about 15,200 tablets) each weighing 50 mg.

Next, in the same manner as in Example 1, a water-soluble pore-forming membrane solution was sprayed on these tablets (350 g) (about 7,000 tablets), and the tablets were dried to give tablets each weighing 56 mg. The controlled release preparation of this invention thus prepared contains emedastine difumarate 4 mg per tablet.

EXAMPLE 12

A mixture of lomerizine hydrochloride (90 g) (see Japanese Patent Publication No. 1323211991), polyvinylalcohol (360 g) (Kuraray Poval PVA-CSTS; Kuraray Co., Ltd.), anhydrous sodium sulfate (360 g) (sieved with Sieve No. 100) and lactose (54 g) was admixed in the fluidized bed granulator, and to the mixture a solution of hydroxypropylcellulose (18 g) in ethanol (342 g) was sprayed as a binder, and the mixture was dried and sieved with Sieve No. 18 to give granules. To the granules (850 g) magnesium stearate (12.1 g) and light anhydrous silicic acid (5.2 g) were admixed and the mixture was compressed by using a rotary tableting machine with a punch 5 mm in diameter to produce uncoated core-tablets 750 g (about 15,000 tablets) each weighing 50 mg.

Next, ethylcellulose (1 weight part) (trade name: Ethocel standard-10; Dow Chemical Co., Ltd.), hydroxypropylmethylcellulose (0.49 weight part) (trade name: TC-5E; Shin-Etsu Chemical Co., Ltd.) and triethyl citrate (0.30 weight part) (trade name: Citroflex 2; Pfizer Co., Ltd.) were dissolved in a mixture of water and ethanol (1:4 weight ratio) so that the concentration of ethylcellulose and hydroxypropylmethylcellulose amounted to 5 weight percentage. This solution was used as a water-soluble pore-forming membrane solution. The above uncoated core-tablets (350 g) (about 7,000 tablets) were put in the tablet coating machine (trade name: Hi-Coater. HCT-MINI; Freund Ind. Co., Ltd.) and on the tablets this water-soluble pore-forming membrane was sprayed and the tablets were dried to produce the coated tablets each weighing 56 mg. The controlled release preparation of this invention thus prepared contains lomerizine hydrochloride 5 mg per tablet.

EXAMPLE 13

In the same manner as in Example 12, a mixture containing lomerizine hydrochloride was compressed by using a rotary tableting machine with a punch 5 mm in diameter to produce uncoated core-tablets (750 g) (about 15,000 tablets) each weighing 50 mg.

Next, on the tablets (350 g) (about 7,000 tablets) in the same manner as in Example 12 except for increasing the coating amount 1 mg per tablet, a water-soluble pore-forming membrane solution was sprayed and the tablets were dried to produce coated tablets each weighing 57 mg. The controlled release preparation of this invention thus prepared contains lomerizine hydrochloride 5 mg per tablet.

EXAMPLE 14

A mixture of lomerizine hydrochloride (90 g), polyvinylalcohol (450 g) (Kuraray Poval PVA-CSTS; Kuraray Co., Ltd.), trisodium citrate dihydrate (270 g) (sieved with Sieve No. 100) and lactose (57.6 g) was admixed in the fluidized bed granulator, and to the mixture a solution of hydroxypropylcellulose (18 g) (trade name: Nisso HPC; Nippon Soda Co., Ltd.) in water (342 g) was sprayed as a binder, and the mixture was dried and sieved with Sieve No. 18 to produce granules. To the granules (855 g) magnesium stearate (7 g) and light anhydrous silicic acid (7 g) were admixed and the mixture was compressed by using a rotary tableting machine with a punch 5 mm in diameter to produce uncoated core-tablets (735 g) (about 14,700 tablets) each weighing 50 mg.

Next, ethylcellulose (1 weight part) (trade name: Ethocel standard-10; Dow Chemical Co., Ltd.), hydroxypropylmethylcellulose (0.47 weight part) (trade name: TC-5E; Shin-Etsu Chemical Co., Ltd.) and triethyl citrate (0.29 weight part) (trade name: Citroflex 2; Pfizer Co., Ltd.) were dissolved in a mixture-of water and ethanol (1:4 weight ratio) so that the concentration of ethylcellulose and hydroxypropylmethylcellulose amounted to 5 weight percent. This solution was used as a water-soluble pore-forming membrane solution. The above uncoated core-tablets 350 g (about 7,000 tablets) were put in the tablet coating machine (trade name: Hi-Coater. HCT-MINI; Freund Ind. Co., Ltd.) and on the tablets the water-soluble pore-forming membrane was sprayed and the tablets were dried to produce coated tablets each weighing 56 mg. The controlled release preparation of this invention thus prepared contains lomerizine hydrochloride 5 mg per tablet.

EXAMPLE 15

In the same manner as in Example 14, a mixture containing lomerizine hydrochloride was compressed by using a rotary tableting machine with a punch 5 mm in diameter to produce uncoated core-tablets 750 g (about 15,000 tablets) each weighing 50 mg.

Next, in the same manner as in Example 16 except for increasing the coating amount 1 mg per tablet, on the tablets 350 g (about 7,000 tablets) a water-soluble pore-forming membrane solution was sprayed, and the tablets were dried to produce coated tablets each weighing 57 mg. The controlled release preparation of this invention thus prepared contains lomerizine hydrochloride 5 mg per tablet.

EXAMPLE 16

A mixture of trazodone hydrochloride (337.5 g) (Japanese Patent Publication 7341/1969), polyvinylalcohol (360 g) (trade name: Kuraray Poval PVA-CSTS; Kuraray Co ., Ltd.) and trisodium citrate dihydrate (180 g) (sieved with Sieve No. 100) was admixed in the fluidized bed granulator, and to the mixture a solution of hydroxypropylcellulose (18 g) (trade name: Nisso HPC; Nippon Soda Co., Ltd.) in water (342 g) was sprayed as a binder, and the mixture was dried and sieved with Sieve No. 18 to produce granules. To the granules (866 g) magnesium stearate (8.7 g) and light anhydrous silicic acid (4.4 g) were admixed and the mixture was compressed by using a rotary tableting machine to produce uncoated core-tablets (750 g) (about 3,700 tablets) each weighing 202 mg.

Next, ethylcellulose (1 weight part) (trade name: Ethocel standard-10; Dow Chemical Co., Ltd.), hydroxypropylmethylcellulose (0.47 weight part) (trade name: TC-5E; Shin-Etsu Chemical Co., Ltd.) and triethyl citrate (0.29 weight part) (trade name: Citroflex 2; Pfizer Co., Ltd.) were dissolved in a mixture of water and ethanol (1:4 weight ratio) so that the concentration of ethylcellulose and hydroxymethylcellulose amounted to 5 weight percent. This solution was used as a water-soluble pore-forming membrane solution. The above uncoated core-tablets (350 g) (about 1,700 tablets) were put in the tablet coating machine (trade name: Hi-Coater. HCT-MINI; Freund Ind. Co., Ltd.) and on the tablets this water-soluble pore-forming membrane solution was sprayed, and the tablets were dried to produce coated tablets each weighing 213 mg. The controlled release preparation of this invention thus prepared contains trazodone hydrochloride 75 mg per tablet.

EXAMPLE 17

In the same manner as in Example 16, a mixture containing trazodone hydrochloride was compressed by using a rotary tableting machine with a punch 8 mm in diameter to produce uncoated core-tablets (750 g) (about 3,700 tablets) each weighing 202 mg.

Next, in the same manner as in Example 16 except for increasing the coating amount 7 mg per tablet, a water-soluble pore-forming membrane solution was sprayed on the uncoated core-tablets (350 g) (about 1,700 tablets) and the tablets were dried to produce tablets each weighing 220 mg. The controlled release preparation of this invention thus prepared contains trazodone hydrochloride 75 mg per tablet.

EXAMPLE 18

Nifedipine (101.4 g) and hydroxymethylcellulose (152 g) (trade name: TC-5E; Shin-Etsu Chemical Co., Ltd.) were dissolved in the mixture of dichloromethane (821 g) and ethanol (547 g) to produce a solid dispersion solution.

A mixture of polyvinylalcohol (810.8 g) (trade name: Kuraray Poval PVA-CSTS; Kuraray Co., Ltd.) and trisodium citrate dihydrate (135.8 g) (sieved with Sieve No. 100) was admixed in the fluidized bed granulator, and to the mixture the above solid dispersion was sprayed, and the mixture was dried and sieved with Sieve No. 30 to give granules. To the granules (592 g) magnesium stearate (3 g) and light anhydrous silicic acid (5 g) were admixed and the mixture was compressed by using a rotary tableting machine with a punch 5 mm in diameter to produce uncoated core-tablets (460 g) (about 7,600 tablets) each weighing 60 mg.

Next, ethylcellulose (1 weight part) (trade name: Ethocel standard-10; Dow Chemical Co., Ltd.), and hydroxypropylmethylcellulose (0.6 weight part) (trade name: TC-5E; Shin-Etsu Chemical Co., Ltd.) were dissolved in the mixture of dichloromethane and ethanol (1:1 weight ratio) so that the total concentration of ethylcellulose and hydroxypropymethylcellulose amounted to 5 weight percent. This solution was used as a water-soluble pore-forming membrane solution. On the above uncoated core-tablets (350 g) (about 5,800 tablets) this water-soluble pore-forming membrane solution was sprayed and the tablets were dried to produce coated tablets each weighing 65 mg. The controlled release preparation of this invention thus prepared contains nifedipine 5 mg per tablet.

EXAMPLE 19

Four controlled release tablets prepared by Example 18 were filled in a hard capsule #2 to produce capsules.

EXAMPLE 20

Nifedipine (338 g) and hydroxypropylmethylcellulose (507 g) (trade name: TC-5E; Shin-Etsu Chemical Co., Ltd.) were dissolved in a mixture of dichloromethane (2,740 g) and ethanol (1,824 g) to produce a solid dispersion solution. A mixture of polyvinylalcohol (2,703 g) (trade name: Kuraray Poval PVA-CSTS; Kuraray Co., Ltd.) and trisodium citrate dihydrate (453 g) (sieved with Sieve No. 100) was admixed in the fluidized bed granulator, and to the mixture the solid dispersion solution was sprayed, and the mixture was dried and sieved with 30 mesh sieve to produce granules. To the granules (3,552 g) magnesium stearate (18 g) and light anhydrous silicic acid (30 g) were admixed and the mixture was compressed by using a rotary tableting machine with a punch 5 mm in diameter to produce uncoated core-tablets (3,420 g) (about 57,000 tablets) each weighing 60 mg.

Next, ethylcellulose (1 weight part) (trade name: Ethocel standard-10; Dow Chemical Co., Ltd.) and hydroxypropylmethylcellulose (0.7 weight part) (trade name: TC-5E; Shin-Etsu Chemical Co., Ltd.) were dissolved in a mixture of dichloromethane and water (1:1 weight ratio) so that the total concentration of ethylcellulose and hydroxypropylmethylcellulose amounted to 5 weight percent to produce a water-soluble pore-forming membrane solution. On the above uncoated core-tablets 350 g (about 5,800 tablets) the water-soluble pore-forming membrane solution was sprayed, and the tablets were dried to produce coated tablets each weighing 65 mg. Hydroxypropylmethylcellulose phthalate [trade name: HPMCP (HP-50); Shin-Etsu Chemical Co., Ltd.] was dissolved in a mixture of dichloroethane and ethanol (1:1 weight ratio) so that the concentration of hydroxypropylmethycellulose phthalate amounted to 5 weight percent, and then the resulting enteric coating solution was sprayed on the coated tablets, and the tablets were dried to produce coated tablets each weighing 68 mg. The controlled release preparation of this invention thus prepared contains nifedipine 5 mg per tablet.

EXAMPLE 21

Four controlled release tablets, preparations prepared by Example 20 were filled in a hard capsule #2 to produce capsules.

EXAMPLE 22

Nifedipine (300 g) and hydroxypropylmethylcellulose (450 g) (trade name: TC-5E; Shin-Etsu Chemical Co., Ltd.) were dissolved in the mixture of dichloromethane (2,432 g) and ethanol (1,624 g) to produce a solid dispersion solution. A mixture of polyvinylalcohol (3,200 g) (trade name: Kuraray Poval PVA-CSTS; Kuraray Co., Ltd.) and trisodium citrate anhydride (536 g) (sieved with Sieve No. 100) was admixed in the fluidized bed granulator, and to the mixture the solid dispersion solution was sprayed and the mixture was dried and sieved with Sieve No. 30 to produce granules. To the granules (4,190 g) magnesium stearate (22.4 g) and light anhydrous silicic acid (37.4 g) were admixed and the mixture was compressed by a rotary tableting machine with a punch 5 mm in diameter to produce uncoated core-tablets (4,000 g) (about 70,000 tablets) each weighing 56.88 mg (Nifedipine 3.75 mg being contained in a tablet).

Next, ethylcellulose (1 weight part) (trade name: Ethocel standard-10; Dow Chemical Co., Ltd.) and hydroxypropylmethylcellulose (0.7 weight part) (trade name: TC-5E; Shin-Etsu Chemical Co., Ltd.) were dissolved in a mixture of dichloromethane and ethanol (1:1 weight ratio) so that the total concentration of ethylcellulose and hydroxypropylmethylcellulose amounted to 5 weight percent to produce a water-soluble pore-forming membrane solution. The above uncoated core-tablets (350 g) (about 6,200 tablets) were put in a coating tablet machine and on them the water-soluble pore-forming membrane solution was sprayed, and the tablets were dried to produce coated tablets each weighing 61.38 mg. Hydroxypropylmethylcellulose phthalate (trade name: HPMCP (HP-50); Shin-Etsu Chemical Co., Ltd.) was dissolved in the mixture of dichloromethane and ethanol (1:1 weight ratio) so that the concentration of the hydroxypropylmethylcellulose phthalate amounted to 5% weight percent, and then the resulting enteric coating solution was sprayed on the above tablets, and the tablets were dried to produce enteric coated tablets each weighing 64.38 mg.

Next, nifedipine (1 weight part) and hydroxypropylmethylcellulose (1.5 weight part) (trade name: TC-5RW; Shin-Etsu Chemical Co., Ltd.) were dissolved in a mixture of dichloromethane and ethanol (6:4 weight ratio) so that the concentration of hydroxypropylmethylcellulose amounted to 5 weight percent to produce a solid dispersion solution. On the above enteric coated tablets this solid dispersion solution was sprayed and the tablets were dried to produce the controlled release tablets of this invention coated with the solid dispersion membrane (corresponding to nifedipine 1.25 mg per tablet) each weighing 67.5 mg. The controlled release preparation of this invention thus prepared contains nifedipine 5 mg per tablet.

EXAMPLE 23

Four controlled release tablets prepared by Example 22 were filled in a hard capsule #2 to produce capsules.

EXAMPLE 24

Nifedipine (90 g) and hydroxypropylmethylcellulose (135.6 g) (trade name: TC-5E; Shin-Etsu Chemical Co., Ltd.) were dissolved in a mixture of dichloromethane (732 g) and ethanol (488 g) to produce a solid dispersion solution. A mixture of polyvinylalcohol (600 g) (trade name: Kuraray Poval PVA-CSTS; Kuraray Co., Ltd.), trisodium citrate anhydride (160.8 g) and crystalline cellulose (trade name: Avicel PH301; Asahi Chemical Ind. Co., Ltd.) was admixed in the fluidized bed granulator, and to the mixture the solid dispersion solution was sprayed, and the mixture was dried and sieved with Sieve No. 30 to produce granules. To this granules (1,088 g) magnesium stearate (6.4 g) and light anhydrous silicic acid (10.7 g) were admixed and the mixture was compressed by a rotary tableting machine with a punch 5 mm in diameter to produce uncoated core-tablets (800 g) (about 15,400 tablets) each weighing 51.9 g (nifedipine 3.75 mg contained per tablet).

Next, ethycellulose (1 weight part) (trade name: Ethocel standard-10; Dow Chemical Co., Ltd.), hydroxypropylmethylcellulose phthalate (0.67 weight part) (trade name: HPMCP (HP-55); Shin-Etsu Chemical Co., Ltd.), and triethyl citrate (0.33 weight part) (trade name: Citroflex 2; Pfizer Co., Ltd.) were dissolved in a mixture of water and ethanol (1:4 weight ratio) so that the total concentration of ethylcellulose and hydroxypropylmethylcellulose phthalate amounted to 5 weight percent to produce a enteric pore-forming membrane solution. The above uncoated core-tablets (350 g) (about 6,700 tablets) were put in the coating tableting machine and on the tablets the enteric pore-forming membrane solution was sprayed, and the tablets were dried to produce tablets coated with the enteric pore-forming membrane each weighing 56.7 mg.

Next, nifedipine (1 weight part) and hydroxypropylmethylcellulose (1.5 weight part) (trade name: TC-5RW; Shin-Etsu Chemical Co., Ltd.) were dissolved in a mixture of dichloromethane and ethanol (6:4 weight ratio) so that the concentration of hydroxypropylmethylcellulose amounted to 5 weight percent to produce a solid dispersion solution. On the above enteric pore-forming membrane coated tablets, the solid dispersion solution was sprayed, and the tablets were dried to produce the controlled release preparation of the invention which was coated with the solid dispersion membrane (containing to nifedipine 1.25 mg per tablet) each weighing 59.85 mg. The controlled release preparation of this invention thus prepared contains 5 mg of nifedipine per tablet.

EXAMPLE 25

Four controlled release tablets prepared by Example 24 were filled in a hard capsule #2 to produce capsules.

EXAMPLE 26

As the same as in Example 8, a mixture containing emedastine difumarate was compressed by a rotary tableting machine with a punch 5 mm in diameter to produce uncoated core-tablets (755 g) (about 15,100 tablets).

Next, ethycellulose (1 weight part) (trade name: Ethocel standard-10; Dow Chemical Co., Ltd.), hydroxypropylmethylcellulose (1 weight part) (trade name: TC-5E; Shin-Etsu Chemical Co., Ltd.), hydroxypropylmethylcellulose phthalate (0.21 weight part) (trade name: HPMCP (HP-55); Shin-Etsu Chemical Co., Ltd.), and triethyl citrate (0.29 weight part) (trade name: Citroflex2; Pfizer Co., Ltd.) were dissolved in a mixture of water and ethanol (1:4 weight ratio) so that the concentration of ethylcellulose, hydroxypropylmethylcellulose and hydroxypropylmethylcellulose phthalate amounted to 5 weight percent to produce a water-soluble enteric pore-forming membrane. The above uncoated core-tablets (350 g) (about 7,000 tablets) were put in the coating tableting machine (trade name: Hi-Coater. HCT-MINI; Freund Ind. Co., Ltd.), and on the tablets this water-soluble pore-forming solution was sprayed and the tablets were dried to produce tablets coated with the water-soluble pore-forming membrane each weighing 56 mg. The controlled release tablet of this invention thus prepared contains emedastine difumarate 4 mg per tablet.

EXAMPLE 27

A mixture containing emedastine difumarate was compressed, in the same manner as in Example 1, to produce uncoated core-tablets and on the surface of the tablets a water-soluble pore-forming solution was sprayed, and the tablets were dried to produce coated tablets with the water-soluble pore-forming membrane (200 g) (about 3,560 tablets) each weighing 56 mg. Hydroxypropylmethylcellulose phthalate (trade name: HPMCP (HP-50); Shin-Etsu Chemical Co., Ltd.) was dissolved in a mixture of ethanol and water (4:1 weight ratio) so that the concentration of hydroxypropylmethylcellulose phthalate amounted to 5 weight percent and the resulting enteric coating solution was sprayed on the tablets, and the tablets were dried to produce tablets coated with the enteric coating membrane each weighing 59 mg. The controlled release tablet thus prepared contains emedastine difumarate 4 mg per tablet.

EXAMPLE 28

In the same manner as in Example 1, a mixture containing emedastine difumarate was compressed to prepare uncoated core-tablets and on the surface of the tablets a water-soluble pore-forming solution was sprayed and the tablets were dried to produce coated tablets with the water-soluble pore-forming membrane (100g) (about 1,780 tablets). Emedastine difumarate (1 weight part), and hydroxypropylmethylcellulose (2 weight parts) (trade name: TC-5MW; Shin-Etsu Chemical Co., Ltd.) were dissolved in a mixture of ethanol and water (1:1 weight ratio) so that the concentration of the hydroxypropylmethylcellulose amounted to 5 weight percent, and the resulting solution was further sprayed on the surface of the coated tablets to produce the controlled release tablets of the invention coated with the solid dispersion membrane (containing emedastine difumarate 1 mg per tablet) each weighing 56 mg. The controlled release preparation thus prepared contains emedastine difumarate 5 mg per tablet.

EXAMPLE 29

In the same manner as in Example 27, a mixture containing emedastine difumarate was compressed to prepare uncoated core-tablets and on the surface of the tablets a water-soluble pore-forming solution and a enteric coating solution were sprayed and the tablets were dried to produce enteric coated tablets (100g) (about 1,690 tablets) each weighing 59 mg. Emedastine difumarate (1 weight part) and hydroxypropylmethylcellulose (2 weight part) (trade name: TC-5MW; Shin-Etsu Chemical Co., Ltd.) were dissolved in a mixture of ethanol and water (1:1 weight ratio) so that the concentration of hydroxypropylmethylcellulose amounted to 5 weight percent and the resulting solid dispersion membrane solution was further sprayed on the surface of the coated tablets, and the tablets were dried to produce tablets which were coated with the solid dispersion membrane (the coated portion corresponding to emedastine difumarate 1 mg per tablet) each weighing 62 mg. The controlled release preparation of this invention thus prepared contains emedastine difumarate 5 mg per tablet.

COMPARATIVE EXAMPLE 11

According with the description in Example 1 of Japanese Patent Publication No. 11699/1994 the procedure was conducted.
A) Core Portion Crystalline nifedipine [average particle seize 3.3 gm (measured by the air permeability method)] (16.5 g) was mixed with lactose (194.0 g) and corn starch (75.0 g), and the mixture was granulated in the paste of corn starch (5.0 g) and hot water (70.0 g), and the resulting granules were dried and sieved and to the granules microcrystalline cellulose (25.0 g) and magnesium stearate (1.0g) were admixed. The mixture was compressed to produce tablets each weighing 63.3 mg with 6 mm in diameter. By coating the tablets with an organic solution of a hydroxypropylmethylcellulose phthalate, there were obtained gastric fluid tolerable coated tablets. The weight of the tablet was 70.3 mg.
B) Granules for Coating Nifedipine (8.4 g) was admixed with lactose (20.2 g), colloidal silica (0.8 g), hydroxypropylcellulose (35.0 g)

(trade name: Nisso HPC (HPC-M); Nippon Soda Co., Ltd.), hydroxypropylcellulose (trade name: Nisso HPC (HPC-L); Nippon Soda Co., Ltd.) (87.4 g) and citric acid (16.0 g) and this mixture was granulated with a solution of hydroxypropylcellulose (1.0 g) in the fluidized bed granulator, dried and sieved. The resulting granules were admixed with magnesium stearate (1.4 g).

The granules thus prepared and the tablets prepared by above A) were together compressed to prepare tablets (10 mm in diameter) each weighing 410 mg.

What is claimed is:

1. A controlled release preparation, comprising:

a coating layer comprising a water-insoluble polymer and at least one selected from the group consisting of a water-soluble polymer and an enteric polymer; and a core member surrounded by the coating layer, comprising a mixture of (a) a mixture of a drug and a water-soluble polymer or a solid dispersion of a drug and a water-soluble polymer, (b) polyvinylalcohol and (c) a salt that is capable of dissolution in gastro-intestinal fluid, wherein the polyvinylalcohol in the core swells in an amount sufficient to burst the coating layer when exposed to gastro-intestinal fluid, the salt that is soluble in gastro-intestinal fluid controlling the swelling of the polyvinylalcohol.

2. A controlled release preparation of claim 1, wherein the coating layer comprises water-insoluble polymer and water-soluble polymer.

3. A controlled release preparation of claim 1, wherein the coating layer comprises water-insoluble polymer and enteric polymer.

4. A controlled release preparation of claim 1, further comprising a second layer comprising enteric polymer on the coating layer.

5. A controlled release preparation of claim 1, further comprising a further coating layer comprising a mixture of a drug and a water-soluble polymer or a solid dispersion of a drug and a water-soluble polymer on the coating layer.

6. A controlled release preparation of claim 1, wherein the coating layer comprises a water-soluble polymer selected from the group consisting of water-soluble cellulose ether, polyvinylpyrrolidone and a mixture thereof.

7. A controlled release preparation of claim 1, wherein the coating layer comprises hydroxypropylmethylcellulose phthalate as an enteric polymer.

8. A controlled release preparation, comprising:

a coating layer comprising ethylcellulose and at least one selected from the group consisting of hydroxypropylmethylcellulose and hydroxypropylmethylcellulose phthalate; and a core surrounded by the coating layer, comprising a mixture of (a) a mixture of a drug and hydroxypropylmethylcellulose or a solid dispersion of a drug and hydroxypropylmethylcellulose, (b) polyvinylalcohol and (c) a salt that is capable of dissolution in gastro-intestinal fluid, wherein the polyvinylalcohol in the core swells in an amount sufficient to burst the coating layer when exposed to gastro-intestinal fluid, the salt that is soluble in gastro-intestinal fluid controlling the swelling of the polyvinylalcohol.

9. A controlled release preparation of claim 8, in the coating layer comprises ethylcellulose and hydroxypropylmethylcellulose.

10. A controlled release preparation of claim 8, wherein the coating layer comprises ethylcellulose and hydroxypropylmethylcellulose phthalate.

11. A controlled release preparation of claim 8, comprising a further coating layer of hydroxypropylmethylcellulose on said coating layer.

12. A controlled release preparation of claim 8, further comprising a further coating layer of a mixture of a drug and hydroxypropylmethylcellulose or a solid dispersion of a drug and hydroxypropylmethylcellulose on said coating layer.

13. A controlled release preparation of claim 1, wherein the core has a diameter of 2–6 mm.

14. A controlled release preparation of claim 13, wherein the diameter is 5 mm.

15. A capsule filled with a controlled release preparation of claim 1.

16. A controlled release preparation of claim 1, wherein the drug is hardly soluble in water.

17. A controlled release preparation of claim 1, wherein the drug is nitedipine.

18. A controlled release preparation of claim 1, wherein the polyvinylalcohol is 93.5–97.5% hydrolized.

19. A controlled release preparation of claim 8, wherein the polyvinylalcohol is 93.5–97.5% hydrolized.

20. A controlled release preparation of claim 1, wherein the salt is selected from the group consisting of trisodium citrate, sodium sulfate and sodium chloride.

21. A controlled release preparation of claim 8, wherein the salt is at least one selected from the group consisting of trisodium, citrate, sodium sulfate and sodium chloride.

* * * * *

UNITED STATES PATENT AND TRADEMARK OFFICE
CERTIFICATE OF CORRECTION

PATENT NO. : 6,156,343
DATED : December 5, 2000
INVENTOR(S) : Morita et al.

Page 1 of 1

It is certified that error appears in the above-identified patent and that said Letters Patent is hereby corrected as shown below:

Column 26, claim 9,
Line 14, "claim 8, in the" should read -- claim 8, wherein the --

Column 26, claim 11,
Lines 20-21, "claim 8, comprising" should read -- claim 8, further comprising --

Column 26, claim 17,
Line 37, "the drug is nitedipine" should read -- the drug is nifedipine --

Column 26, claim 21,
Line 48, "trisodium, citrate" should read -- trisodium citrate --

Signed and Sealed this

First Day of January, 2002

Attest:

Attesting Officer

JAMES E. ROGAN
Director of the United States Patent and Trademark Office